(12) United States Patent
Nakaishi et al.

(10) Patent No.: US 9,974,288 B2
(45) Date of Patent: May 22, 2018

(54) METHOD OF MAKING POLYETHYLENE GLYCOL-MODIFIED MAMMALIAN ERYTHROPOIETIN IN A TRANSGENIC CHICKEN

(71) Applicant: KANEKA CORPORATION, Osaka (JP)

(72) Inventors: Tomoyuki Nakaishi, Himeji (JP); Takuya Shindo, Kobe (JP); Tomoko Awa, Takasago (JP)

(73) Assignee: Kaneka Corporation, Osaka (JP)

( * ) Notice: Subject to any disclaimer, the term of this patent is extended or adjusted under 35 U.S.C. 154(b) by 0 days. days.

(21) Appl. No.: 15/207,850

(22) Filed: Jul. 12, 2016

(65) Prior Publication Data

US 2016/0353717 A1 Dec. 8, 2016

Related U.S. Application Data

(62) Division of application No. 12/065,450, filed as application No. PCT/JP2006/317124 on Aug. 30, 2006, now abandoned.

(30) Foreign Application Priority Data

Aug. 31, 2005 (JP) ................................ 2005-251128

(51) Int. Cl.
| | |
|---|---|
| G01N 33/00 | (2006.01) |
| A01K 67/027 | (2006.01) |
| C07K 14/505 | (2006.01) |
| C12N 15/85 | (2006.01) |
| A61K 38/18 | (2006.01) |
| C07K 14/005 | (2006.01) |
| C12N 7/00 | (2006.01) |
| C12N 15/86 | (2006.01) |
| A61K 47/60 | (2017.01) |
| A61K 38/00 | (2006.01) |

(52) U.S. Cl.
CPC ...... *A01K 67/0275* (2013.01); *A61K 38/1816* (2013.01); *A61K 47/60* (2017.08); *C07K 14/005* (2013.01); *C07K 14/505* (2013.01); *C12N 7/00* (2013.01); *C12N 15/8509* (2013.01); *C12N 15/86* (2013.01); *A01K 2217/05* (2013.01); *A01K 2217/052* (2013.01); *A01K 2227/30* (2013.01); *A01K 2267/01* (2013.01); *A01K 2267/02* (2013.01); *A61K 38/00* (2013.01); *C12N 2015/8518* (2013.01); *C12N 2740/10043* (2013.01); *C12N 2740/10052* (2013.01); *C12N 2760/20222* (2013.01); *C12N 2799/027* (2013.01); *C12N 2830/008* (2013.01)

(58) Field of Classification Search
USPC ...................... 435/325; 800/3, 19
See application file for complete search history.

(56) References Cited

U.S. PATENT DOCUMENTS

| | | | | |
|---|---|---|---|---|
| 6,340,742 | B1 * | 1/2002 | Burg | C07K 14/505 |
| | | | | 424/85.1 |
| 6,472,509 | B1 | 10/2002 | Imamura et al. | |
| 6,518,045 | B1 | 2/2003 | Imamura et al. | |
| 6,730,822 | B1 * | 5/2004 | Ivarie | A01K 67/0275 |
| | | | | 435/320.1 |
| 7,812,215 | B2 * | 10/2010 | Harvey | A01K 67/0275 |
| | | | | 800/19 |
| 2002/0107366 | A1 | 8/2002 | Imamura et al. | |
| 2004/0019922 | A1 | 1/2004 | Ivarie et al. | |
| 2004/0019923 | A1 | 1/2004 | Ivarie et al. | |
| 2004/0172666 | A1 | 2/2004 | Iijima et al. | |
| 2005/0002260 | A1 | 1/2005 | Koyama | |
| 2007/0214511 | A1 | 9/2007 | Yamashita et al. | |

FOREIGN PATENT DOCUMENTS

| | | | |
|---|---|---|---|
| EP | 1013288 A2 * | 11/1999 | |
| EP | 1013288 A2 | 6/2000 | |
| EP | 1333036 A1 * | 9/2001 | |
| EP | 1 333 036 A1 | 8/2003 | |
| JP | 2001-520009 A | 10/2001 | |
| JP | 2002-176880 A | 6/2002 | |
| JP | 2003-503464 A | 1/2003 | |
| JP | 2003-339261 A | 12/2003 | |
| JP | 2004-236626 A | 8/2004 | |
| WO | 1997/46583 A1 | 12/1997 | |
| WO | 99/19472 A1 | 4/1999 | |
| WO | 2001/02017 A2 | 1/2001 | |
| WO | WO 01/02017 * | 1/2001 | |
| WO | 2004/047858 A1 | 6/2004 | |

(Continued)

OTHER PUBLICATIONS

Lillico (Drug Discovery Today, Feb. 2005, vol. 10, No. 3, p. 191-196).*
Love (Bio/Technology, 1994, vol. 12, p. 60-63).*
Sang (TibTech, 1994, vol. 12, p. 415-420).*
Thoroval (Transgenic Research, 1995, vol. 4, p. 369-376).*
Mohammed (1998, Immunotechnology, vol. 4, p. 115-125).*
Harvey (Nature Biotech, Apr. 2002, vol. 19, p. 396-399).*
Ivarie (Trends in Biotechnology, Jan. 2003, vol. 21, p. 14-19).*
Bird Classification/Families of the Eastern US Birds, 2009.*
Baldwin et al., Transient and stable transfection of Chinese hamster ovary cells with the recombinant feline erythropoietin gene and expression, purification, and biological activity of feline erythropoietin protein.

(Continued)

*Primary Examiner* — Michael C Wilson
(74) *Attorney, Agent, or Firm* — Osha Liang LLP

(57) ABSTRACT

The present invention provides to a polyethylene glycol-modified feline-derived protein which is obtained by chemically modifying a feline-derived protein with polyethylene glycol. The feline-derived protein is produced by a method comprising any or a combination of extracting the protein from somatic cells of a transgenic bird and/or an egg laid thereby, purifying and activating the same. The transgenic bird has a foreign gene containing a sequence encoding a feline-derived protein.

9 Claims, 5 Drawing Sheets

(56) References Cited

FOREIGN PATENT DOCUMENTS

| WO | 2004/067713 A2 | 8/2004 |
|---|---|---|
| WO | 2005/065450 A1 | 7/2005 |
| WO | 2006/082517 A1 | 8/2006 |

OTHER PUBLICATIONS

DDBJ/EMBL/GenBank [online], Accesion No. NP_001009269, <http://www.nebi.nlm.nih.gov/entrez/viewer.fcgi?db=protein &val=57163805> Apr. 16, 2005 uploaded, Retrieved on Sep. 13, 2006, Wen Danyi, et al., Definition: erythropoietin [Felis catus].

Fee, Conan J., et al., "PEG-proteins: Reaction engineering and separation issues" Chemical Engineering Science, vol. 61, No. 3, Feb. 1, 2006, pp. 924-939, XP025012432.

Lillico et al., "Transgenic chickens as bioreactors for protein-based drugs", Drug Discover Today, Elsevier, Rahway, NJ, US, vol. 10., No. 3, Feb. 1, 2005, pp. 191-196, XP004748154.

M. Uehira, "Retrovirus Vector ni yoru Transgenic Chorui Sakusei ni Okeru Donyu Jiki no Kento," The Society of Chemical Engineers, Japan Dai 70 Nenkai (2005), Kenkyu Happyo Koen Yoshishu, Feb. 22, 2005, p. 325.

Nishimura, Y. et al., "Molecular cloning and sequencing of feline stromal cell-derived factor 1a and B", European Journal of Immunogenitics, vol. 25, No. 4, Jan. 1, 1998, pp. 303-305, XP009080019.

R.L. Klein, et al., "Measurements of Vector-Derived Neurotrophic Factor and Green Fluorescent Protein Levels in the Brain," Methods, 2002, pp. 286-292, vol. 28.

Thoraval, Pierrick, et al., "Germline transmission of exogenous genes in chickens using helper-free ecotropic avian leukosis virus-based vectors", Transgenic Research, 4, 369-376 (1995).

Sang, Helen, "Transgenic chickens—methods and potential applications", Tib Tech, vol. 12, p. 415-420, (1994).

Proudman, J. A., "The quest for transgenic poultry: birds are not mice with feathers", Biotechnology in Animal Husbandry, vol. 5, Kluwer Academic Publishers, p. 283-299, (2001).

Mohammed, S. Mansoor, "Deposition of genetically engineered human antibodies into the egg yolk of hens", Immunotechnology, vol. 4, p. 115-125, (1998).

Mizuarai, Shinji, et al., "Production of Transgenic Quails with High Frequency of Germ-Line Transmission Using VSV-G Pseudotyped Retroviral Vector", Biochemical and Biophysical Res., Comm., vol. 286, p. 456-463, (2001).

Love, Jamie, et al., "Transgenic Birds by DNA Microinjection", Bio/Technology, vol. 12 p. 60-63, (1994).

Ivarie, Roberts, "Avian transgenesis: progress towards the promise", Trends in Biotechnology, vol. 21, Jan. 2003, p. 14-19.

Harvey, Alex J., "Expression of exogenous protein in the egg white of transgenic chickens", Nature Biotech, Apr. 2002, vol. 19, p. 396-399.

Lillico, Simon, G., et al., "Transgenic chickens as bioreactors for protein-based drugs", Drug Discovery Today, vol. 10, No. 3, p. 191-196, (2005).

Human EPO, 2013.

Feline EPO, 2013.

\* cited by examiner

\*  : P＜0.05   \*\* : P＜0.01   \*\*\* : P＜0.001
Each point and bar represents the mean ±SD for fine animals.

METHOD OF MAKING POLYETHYLENE GLYCOL-MODIFIED MAMMALIAN ERYTHROPOIETIN IN A TRANSGENIC CHICKEN

CROSS REFERENCE TO RELATED APPLICATIONS

This is a Divisional application of U.S. application Ser. No. 12/065,450, filed Jan. 13, 2009, which is a National Stage of International Application No. PCT/JP2006/317124 filed on Aug. 30, 2006, claiming priority based on Japanese Patent Application No. 2005-251128, filed Aug. 31, 2005, the contents of all of which are incorporated herein by reference in their entirety.

TECHNICAL FIELD

The present invention relates to a method of producing a transgenic bird containing a foreign gene as transferred into the genome thereof and to the expression of a feline-derived protein in such transgenic bird. More particularly, it relates to the expression of feline-derived erythropoietin in such transgenic bird.

BACKGROUND ART

In recent years, a number of proteins have come into use as pharmaceuticals. This is because the gene recombination technology has been developed for and applied to the introduction or transfer of a gene coding for a desired protein into microorganisms or mammalian cells, so that commercial protein production is now feasible by cultivating the thus-produced genetically modified organisms. For such a medicinal protein to show the physiological activity or activities intrinsic therein, posttranscriptional modifications, for example folding, glycosylation and disulfide bond formation is necessary as in nature.

Methods of producing proteins by cultivating microorganisms are capable of producing proteins at low costs since microorganisms can grow rapidly and medium compositions therefor are simple. However, in many cases, due posttranscriptional modifications of the desired protein are not made properly in microorganisms. Therefore, it is difficult to obtain a protein having the same physiological activity as that of the natural counterpart in sufficient quantities; in the existing circumstances, it is still a long way to practical use of such protein production methods on a commercial basis.

Therefore, it is the mainstream of the art to introduce a gene for a desired protein into mammalian cells and cultivating the cells to cause them to product the protein. Such pharmaceutical proteins as blood coagulation factors, thrombolytic agents and antibodies for pharmaceutical use as produced using recombinant mammalian cells are already on the market and used. However, those methods which use mammalian cells have a problem in that culture tanks and medium for exclusive use are required and the production cost is high.

To overcome these problems, animal factories have now attracted attention. The technology concerned comprises using gene-transferred (transgenic) animals to produce desired proteins. Attempts have been made to produce transgenic mammals using goats, sheep and cows, among others, and cause the production of the desired proteins in the milks thereof. Thus, there is a report describing the expression of an antibody at a level of 10 mg/ml in milk, although the expression level varies depending on the protein species (cf. e.g. Non-Patent Document 1). However, this technology has the BSE (bovine spongiform encephalopathy) problem and other problems; utilizable mammalian individuals are large-sized and, therefore, are difficult to produce, raise and handle; a further problem is that the period from birth to sexual maturation is long, namely 8 months in goats or sheep, or 15 months in cows.

Therefore, investigations have been made to use transgenic birds for the expression of a desired protein in eggs thereof. This technology has several advantages: the egg-laying productivity is high, there is no BSE problem, the maturation period is short (5 months in chickens), individuals are small in size and therefore a large number of individuals can be raised, the technique of artificial insemination has been established, enabling rapid raising of large-scale transgenic groups, and the egg inside is generally sterile by nature.

As for the methods of producing transgenic birds, the method using a retrovirus vector, the method using embryonic stem cells, the method using primordial germ cells and the method comprising causing a target gene to adhere to spermatozoa for introduction thereof, among others, are under investigation. Among those methods, the method using a retrovirus vector is the commonest. So far, a study in which an avian leukemia virus (ALV)-derived replication defective retrovirus vector was used has been reported (cf. e.g. Patent Document 1). The target protein used was β-lactamase, and the promoter gene used was the cytomegalovirus (CMV) promoter gene. Transgenic birds were produced successfully by retrovirus vector introduction into blastoderms at the stage X just after egg laying. Reportedly, the level of expression was 0.33 mg/ml (the egg white volume being estimated at 40 ml) as determined by western blot analysis and, when expressed in terms of β-lactamase activity, it was 0.003 to 0.033 mg/ml. On that occasion, the frequency of appearance of G0 transgenic chimeric birds was 20%. The result of an investigation of the efficiency of introduction into germ cells indicated that about 5% of male G0 transgenic chimeric birds had the transgene in spermatozoa. According to another report about a similar experiment, the transgene expression was about 1.2 µg/ml of egg white in G2 birds having the transgene introduced in the whole body (cf. e.g. Non-Patent Document 2). On that occasion, the frequency of appearance of G1 from G0 was 3/422 (0.71%).

Further, there are reports about transgenic birds expressing human interferon or human-derived erythropoietin (cf. e.g. Patent Document 2 and 3). Interferon is a glycoprotein having a molecular weight of about 20,000 which is produced and secreted by almost all animal cells on the occasion of viral infection; it is also known as virus inhibiting factor. Erythropoietin (EPO) is a sugar chain-rich polypeptide mainly produced in the kidney and capable of acting on precursor cells in the hemopoietic tissue to promote the differentiation thereof into and the growth of erythrocytes. Currently, recombinant human EPO produced by the recombinant DNA technology using animal cells as hosts is on the market and is used mainly as a therapeutic agent for various types of anemia, typically renal anemia resulting from nephropathy-associated reduced EPO productivity. When an ALV-derived replication defective retrovirus vector and the CMV promoter gene or ovomucoid-ovotransferrin fused promoter gene were used, human interferon was expressed in serum at a maximum level of 200 ng/ml, and human-derived erythropoietin in serum and egg white each at a maximum level of 70 ng/ml.

In another report, it is reported that high levels of virus titer, infectivity and expression were obtained using the mouse stem cell virus (MSCV) vector and VSV-G envelope (cf. e.g. Patent Document 4). Further, according to that report, high expression levels were realized by adjusting the time of retrovirus vector introduction and, when an antiprion single chain antibody (scFv) is used as the target protein, high levels of expression of 0.5 to 1 mg/ml in egg white and in egg yolk were realized.

Cats are animals long loved as pets by humans and recently have been establishing their position as the so-called "partner, companion or friend animals" in the human society. On the other hand, in the fields of medicine, pharmacology, veterinary medicine and psychology, among others, cats have so far been used as experimental animals and recently have come into use in testing pharmaceuticals for safety and efficacy. In view of the circumstances in which the social importance of cats is increasing, feline diseases and infections are objects of concern and effective therapeutic means therefor are desired. In recent years, medicinal proteins have attracted attention in the treatment of feline diseases as well and, currently, medicinal proteins for human use are mainly used in cats as well. However, medicinal proteins for human use differ in amino acid sequence from in vivo proteins intrinsic in cats and, therefore, may possibly differ in effect or efficacy in living cats. Further, the difference in amino acid sequence may possibly cause an allergic reaction and, in the worst case, an anaphylactic symptom. Thus, such proteins cannot be used in high-frequency dosage regimens, so that the development of medicinal proteins intrinsic in cats is demanded.

As the feline-derived medicinal proteins so far studied widely, there may be mentioned cytokines. Cytokines are proteinic factors which are released from cells and mediate intercellular interactions in the exertion of immune or inflammatory response modulating, antiviral, antitumor, and cell proliferation and differentiation regulating actions. As the feline-derived cytokines so far reported, there may be mentioned erythropoietin (cf. e.g. Non-Patent Document 3 and 4) and interleukin 12 (cf. e.g. Patent Document 5), among others. As regards the production of these, mammalian cells have so far been used; under the existing circumstances, any transgenic birds have been used in such production.

Patent Document 1: Japanese Kohyo Publication 2001-520009
Patent Document 2: United States Patent Application Publication 2004/0019922
Patent Document 3: United States Patent Application Publication 2004/0019923
Patent Document 4: Japanese Kokai Publication 2002-176880
Patent Document 5: International Publication WO 97/046583
Non-Patent Document 1: Trends Biotechnol. 1999, Sep.; 17(9):367-74
Non-Patent Document 2: Nat. Biotechnol. 2002, Apr.; 20(4):396-9
Non-Patent Document 3: Blood, 1993, Sep. 1; 82(5):1507-16
Non-Patent Document 4: Vet. Immunol. Immunopathol. 1986, Jan.; 11(1):1-19

SUMMARY OF THE INVENTION

No examples have so far been reported of the expression of a feline-derived protein using transgenic birds. In higher animals, proteins after translation undergo various modifications such as folding, glycosylation and disulfide bond formation so that they may acquire respective specific, physiologically active forms. The protein modification varies depending on the tissue in one and the same individual. It is therefore very difficult to obtain a high level of expression of a foreign gene in animal cells. For example, on the occasion of producing a medicinal protein by cultivation of mammalian cells, an appropriate cell line suited for the production of the medicinal protein from among various animal species and tissues is to be selected. While human-derived proteins have so far been produced using transgenic birds, the human and cat taxonomically belong to different orders; this is a great difference. Even in the case of human and feline counterpart proteins having one and the same activity, they differ in amino acid sequence. In the case of erythropoietin, the amino acid homology between human and cat is about 83%. Further, since there is a difference in sugar chain sequence between human and cat, it is difficult to say that what was possible with a human-derived protein is also possible with the corresponding feline-derived protein. Accordingly, it is an object of the present invention to teach a method producing a feline-derived protein in transgenic birds.

The present inventors paid their attention to feline-derived cytokines as the feline-derived proteins and employed feline-derived erythropoietin, one of the feline-derived cytokines, as the target. It is an object of the present invention to teach a method of producing feline-derived erythropoietin in transgenic birds, in particular. The human-derived erythropoietin-producing transgenic birds disclosed in United States Patent Application Publications 2004/0019922 and 2004/0019923 have a problem in that the erythropoietin production is low. Accordingly, it is an object of the present invention to provide a transgenic bird capable of producing erythropoietin at high concentration levels and a method of producing the same.

A characteristic feature of the present invention consists in a transgenic bird with a foreign gene containing a feline-derived protein-encoding sequence as transferred therein and in a method of producing the same. Another characteristic feature of the invention consists in a transgenic bird having a foreign gene containing a sequence coding for a feline-derived cytokine protein and/or a protein substantially identical in biological activity thereto and in a method of producing the same. A further characteristic feature of the invention consists in a transgenic bird having a foreign gene containing at least a part of a sequence coding for feline-derived erythropoietin identified under SEQ ID NO: 1 in the sequence listing and/or a sequence coding for a protein substantially identical in biological activity to feline-derived erythropoietin and in a method of producing the same. A characteristic feature of the invention consists in a transgenic bird having a foreign gene containing a sequence coding for feline-derived erythropoietin identified under SEQ ID NO:1 in the sequence listing and/or a sequence coding for a protein substantially identical in biological activity to feline-derived erythropoietin and in a method of producing the same.

The present invention is further characterized in that a replication defective retrovirus vector is used in producing transgenic birds. The invention is also characterized in that the replication defective retrovirus vector contains a Moloney murine leukemia virus- and/or Moloney murine sarcoma virus-derived sequence. The invention is further characterized in that the replication defective retrovirus vector contains a murine stem cell virus (MSCV)-derived sequence, thus enabling use of a virus highly capable of infecting germ cells and stem cells. The invention is also characterized in that the replication defective retrovirus vector contains the VSV-G envelope and, in this respect, a wide range of mammalian and non-mammalian cells, including cells hardly allowing transduction, can be infected therewith.

Further, the invention is characterized in that transgenic birds are produced using a replication defective retrovirus vector containing a non-tissue-specific promoter gene. The invention is further characterized in that the non-tissue-specific promoter gene contains a part or the whole of the chicken β-actin promoter gene.

The invention is further characterized in that transgenic birds are produced using a replication defective retrovirus vector containing a tissue-specific promoter gene. The invention is further characterized in that the replication defective retrovirus vector contains a tissue-specific promoter gene containing a part or the whole of an oviduct-specific promoter gene. The invention is further characterized in that the oviduct-specific promoter gene comprises at least a part or the whole, or a combination, of the ovalbumin, ovotransferrin, ovomucoid, ovomutin, lysozyme, G2 globulin, G3 globulin, ovoinhibitor, ovoglycoprotein, ovoflavoprotein, ovomacroglobulin, cystatin and/or avidin promoter gene.

The invention is further characterized in that transgenic birds are produced using a replication defective retrovirus vector containing a transcriptional enhancer and/or regulatory element. The invention is further characterized in that the regulatory element contains apart or the whole of the woodchuck posttranscriptional regulatory element sequence.

The invention is further characterized in that transgenic birds are produced by a method which comprises infecting avian embryos with a replication defective retrovirus vector containing a foreign gene and hatching the embryos. The invention is further characterized in that transgenic birds are produced by a method which comprises incubating fertilized avian eggs, infecting the embryos after at least 24 hours of incubation with a replication defective retrovirus vector containing a foreign gene and hatching the embryos. More preferably, it is characterized in that the embryos to be infected with the replication defective retrovirus vector containing a foreign gene are those formed not earlier than 32 hours but not later than 72 hours after the start of incubation. Still more preferably, it is characterized in that the embryos to be infected with the replication defective retrovirus vector containing a foreign gene are those formed not earlier than 48 hours but not later than 64 hours after the start of incubation. The invention is further characterized in that the method of infecting with a replication defective retrovirus vector containing a foreign gene comprises microinjection into the heart or blood vessel formed in the embryo.

The invention is further characterized in that the transgenic bird is one derived from a domestic fowl. More preferably, it is characterized in that the transgenic bird is one derived from a chicken.

The invention is further characterized in that it covers transgenic birds, descendants thereof, eggs thereof and/or spermatozoa thereof and comprises any of the methods of producing transgenic birds as mentioned above.

The invention is further characterized in that it is directed to a method of producing a foreign gene-derived protein which comprises the steps of extracting that protein from the blood, somatic cells and/or eggs of the transgenic bird, purifying and activating the same, either singly or in combination, and comprises any of the methods of producing transgenic birds as mentioned above.

The present invention also relates to a polyethylene glycol-modified feline-derived protein obtained by chemically modifying, with polyethylene glycol, the feline-derived protein produced in the manner mentioned above.

Preferably, the feline-derived protein comprises a feline-derived cytokine and/or a protein substantially identical in biological activity thereto. More preferably, the feline-derived protein comprises a protein containing at least apart of feline-derived erythropoietin identified under SEQ ID NO:1 in the sequence listing and/or of a protein substantially identical in biological activity thereto. Still more preferably, the feline-derived protein comprises feline-derived erythropoietin identified under SEQ ID NO:1 in the sequence listing and/or a protein substantially identical in biological activity thereto.

The invention is further characterized in that the polyethylene glycol to be used for the modification of the feline-derived protein has a weight average molecular weight of 5 to 40 kDa. More preferably, the polyethylene glycol has a weight average molecular weight of 20 kDa.

The present invention also relates to a polyethylene glycol-modified feline-derived protein in which the number of polyethylene glycol molecules added is 1 or 2 or more and which has an apparent molecular weight of from 100 kDa to 900 kDa per polyethylene glycol-modified molecule as determined by gel filtration column chromatography in an aqueous solvent. Preferably, the polyethylene glycol addition number is 1 and the apparent molecular weight per polyethylene glycol-modified molecule as determined by gel filtration column chromatography in an aqueous solvent is from 100 kDa to 500 kDa.

The present invention further relates to a polyethylene glycol-modified feline-derived protein composition which comprises the above-mentioned polyethylene glycol-modified feline-derived protein.

The invention also relates to a medicinal composition for feline use which comprises the above-mentioned polyethylene glycol-modified feline-derived protein or polyethylene glycol-modified feline-derived protein composition as an active ingredient. The medicinal composition has feline erythropoietin activity and prolonged action and is suited for use in the treatment of feline renal anemia.

The present invention further relates to a method of producing a polyethylene glycol-modified feline-derived protein composition which comprises causing a polyethylene glycol succinimidyl ester derivative to add to a feline-derived protein.

DETAILED DESCRIPTION OF THE INVENTION

In the following, the present invention is described in detail.

The term "protein" means a product derived from two or more amino acids by peptide bonding and generally includes peptides as well as oligopeptides shorter in chain length. The amino acid or acids may be modified. For protein secretion, it is preferred that the protein be provided with a secretory signal sequence. The secretory signal is not necessarily an autologous sequence.

The foreign gene is not particularly restricted but includes not only non-avian genes but also avian ones. Even a sequence intrinsic in an individual subjected to transgenic production is referred to as foreign gene since a gene is newly introduced into the genome intrinsic in that individual.

In the practice of the invention, the foreign gene contains a feline-derived protein-encoding sequence and the limits of the coding sequence are defined by the 5'-terminal initiation codon and the 3'-terminal termination codon corresponding to the initiation codon. The vicinity of the 5'-terminal initiation codon preferably contains Kozak's consensus sequence. Preferably, there is a ribosome-binding site upstream of the coding sequence.

The foreign gene may contain a nontranslatable region in addition to the feline-derived protein-encoding sequence mentioned above.

The feline-derived protein is not particularly restricted but preferably comprises a feline-derived cytokine protein and/or a protein substantially identical in biological activity thereto. A cytokine is a proteinic factor released from cells and mediating intercellular interactions in the exertion of immune or inflammatory response modulating, antiviral, antitumor, and cell proliferation and differentiation regulating actions, among others; as specific examples, there may be mentioned various interleukins, interferon α, β and γ, tumor necrosis factor, lymphotoxin, colony-stimulating factor and erythropoietin, which are hematopoietic factors, and epidermal growth factor and fibroblast growth factor, which are growth factors. In the practice of the invention, a protein containing at least a part of feline-derived erythropoietin identified under SEQ ID NO:1 in the sequence listing and/or of a protein substantially identical in biological activity thereto is more preferred, and the whole of feline-derived erythropoietin identified under SEQ ID NO:1 in the sequence listing and/or of a protein substantially identical in biological activity thereto is still more preferred.

In the present specification, the "protein substantially identical in biological activity", in the case of a cytokine, for instance, means a protein resulting from deletion, addition or substitution of 1 to 10 amino acid residues in the amino acid sequence of the feline-derived cytokine protein and retaining the physiological activity of the cytokine. When the protein has the same physiological activity, it is regarded as substantially identical in biological activity, irrespective of intensity of activity.

The region from the first to the 26th amino acid residues in SEQ ID NO:1 is the so-called signal peptide and is eliminated by cleavage on the occasion of secretion. Therefore, it is a region little influencing the biological activity of feline-derived erythropoietin. The feline-derived protein obtained in accordance with the invention may have an amino acid sequence resulting from deletion, addition or substitution of 1 to 10 amino acid residues in the amino acid sequence starting from the 27th amino acid residue in the amino acid sequence shown under SEQ ID NO:1 in the sequence listing.

In producing the transgenic bird according to the invention, a retrovirus vector is preferably used. The retrovirus vector includes, within the meaning thereof, different forms, namely plasmid, virus particles and packaging cells. Packaging cells are cells resulting from introduction thereinto of a gene coding for at least one of the proteins necessary for the replication of virus particles.

From the safety viewpoint, the retrovirus vector to be used in the practice of the invention is preferably a replication defective one. The method of rendering the retrovirus replication defective preferably comprises deleting at least a part or the whole of each coding sequence or a sequence necessary for the expression thereof so that one or a combination of the protein (group specific antigen, gag), which is contained in the internal core, reverse transcriptase (polymerase, pol) and envelope glycoprotein (envelope, env), which are necessary for virus particle replication, may not be expressed, or causing a mutation or mutations by substitution and/or insertion so that the sequences mentioned above may not be expressed. Since the length of a gene that can be inserted into a retrovirus vector is limited depending on the viral species, mutations by deletion are preferred and, from the viewpoint of safety and of increased insert fragment length, it is preferred that a plurality of gag, pol and env be deleted. Preferably, the retrovirus vector contains a viral packaging signal (phi) which functions as a landmark of packaging in the virus particle. Since a part of the gag region may sometimes function as a viral packaging signal, it is preferred, from the increased virus titer viewpoint, that the viral vector contain at least a part of the gag region rendered incapable of being expressed (J. Virol. 1987, May; 61(5): 1639-46).

The retrovirus is not particularly restricted but includes viruses derived from Moloney murine leukemia virus, Moloney murine sarcoma virus, avian leukemia virus (ALV) and human immunodeficiency virus (HIV), among others. While Moloney murine leukemia virus and/or Moloney murine sarcoma virus is preferred, viruses highly capable of infecting germ cells and stem cells, such as murine stem cell virus (MSCV) and murine embryonic stem cell virus (MESV), are preferably used for the infection of the avian embryo. MSCV is more preferred. The replication defective retrovirus vector to be used in the practice of the invention preferably contains a sequence derived from such a virus as mentioned above. For efficient infection of avian cells with such virus vector, the coat protein is preferably replaced artificially with the bovine vesicular stomatitis virus-derived VSV-G envelope protein, although the retrovirus vector is not limited to this type of virus.

The replication defective retrovirus vector to be used in the practice of the invention preferably contains at least a part or the whole of an appropriate promoter gene for the expression of the foreign gene in avian cells. The promoter gene is a region on a DNA or RNA which determines the transcription initiation site on a gene or directly regulating the frequency thereof.

The replication defective retrovirus vector to be used in the practice of the invention preferably contains a non-tissue-specific promoter gene or a tissue-specific promoter gene.

A tissue-specific promoter gene is a promoter gene showing especially intense activity in a certain specific avian tissue or cells. By using a tissue-specific promoter gene, it becomes advantageously possible to reduce or eliminate the possibility of the expression of a desired protein adversely affecting the development or survival of birds.

The tissue-specific promoter gene is not particularly restricted but includes oviduct-specific promoter genes. The oviduct tissue becomes active after sexual maturation and therefore is strongly induced after sexual maturation in many cases.

As the oviduct-specific promoter gene, there may be mentioned the ovalbumin, ovotransferrin, ovomucoid, ovomutin, lysozyme, G2 globulin, G3 globulin, ovoinhibitor, ovoglycoprotein, ovoflavoprotein, ovomacroglobulin, cystatin and avidin promoter genes of the avian origin, among others. The use of these oviduct-specific promoter genes is particularly preferred since the desired protein can then be expressed in egg white at high levels.

The non-tissue-specific promoter gene is a promoter gene which is not a tissue-specific promoter gene. The non-tissue-specific promoter gene is not particularly restricted but includes those active in almost all avian somatic cells. In that case, the desired protein is expressed in blood as well and therefore the expression or non-expression thereof can advantageously be detected in the stage of nestlings.

The non-tissue-specific promoter gene is not particularly restricted but includes such virus-derived promoter genes as the β-actin promoter gene, EF1α promoter gene, thymidine kinase promoter gene, simian virus 40 (SV40) promoter gene, cytomegalovirus (CMV) promoter gene, and Rous sarcoma virus (RSV) promoter gene. In addition, such a non-tissue-specific inducible type promoter gene as the tetracycline inducible promoter gene may also be used. As far as the non-tissue-specific promoter gene is concerned, the retrovirus vector preferably contains a part or the whole of the avian β-actin promoter gene.

The replication defective retrovirus vector to be used in the practice of the invention may contain a transcription enhancer and/or regulatory element. The transcription enhancer is a sequence promoting the transcription from a promoter gene but is a region on DNA or RNA which by itself cannot cause transcription. A transcription enhancer, even when connected to a promoter gene different from the one for which it originally functions, can function in many instances, so that the combination thereof with the promoter gene is not limited. The transcription enhancer is not particularly restricted but includes the SV40, CMV and thymidine kinase enhancers, steroid responsive element and lysozyme enhancer, among others. The regulatory element is a region on DNA or RNA which contributes to transcriptional regulation and RNA stabilization after transcription but by itself cannot cause transcription. The regulatory element is not particularly restricted but includes the woodchuck posttranscriptional regulatory element (WPRE; U.S. Pat. No. 6,136,597), among others.

The retrovirus vector contains at least a part of a long terminal repeat (LTR) at each of the 5' terminus and 3' terminus. The LTR contains a transcriptional promoter gene and a polyA addition signal and therefore can be utilized as a promoter gene or a terminator gene. In the retrovirus vector, the target protein-encoding sequence, promoter gene, transcription enhancer and/or regulatory element are contained between the 5' LTR and 3' LTR. When a promoter other than LTR is used, the retrovirus vector preferably has a structure such that the target protein-encoding sequence is connected to a site downstream from the promoter. For the retrovirus vector to be transcribed for the construction of virus particles, it is preferred that no terminator or polyA signal be contained between the 5' LTR and 3' LTR.

The retrovirus vector to be used in the practice of the invention may contain a marker gene. The marker gene is a gene coding for a protein serving as a landmark in the identification and isolation of correctly gene-transferred cells. The marker gene is not particularly restricted but includes genes for fluorescent proteins such as green fluorescent protein (GFP), cyan fluorescent protein (CFP) and luciferase; drug resistance genes such as the neomycin resistance (Neo$^r$), hygromycin resistance (Hyg$^r$) and puromycin resistance (Puro$^r$) genes; and, further, the thymidine kinase, dihydrofolate reductase, aminoglycoside phosphotransferase, chloramphenicol acetyl transferase, β-lactamase and β-galactosidase genes, among others. The marker gene is preferably accompanied by a promoter gene and an element necessary for the expression thereof.

Now, mention is made of a preferred mode of embodiment of the method of preparing a replication defective retrovirus vector suited for use in the practice of the invention.

The replication defective retrovirus vector to be used in the practice of the invention is lacking in the gag, pol and env genes necessary for the replication thereof. A replication defective retrovirus vector plasmid enabling the expression of the desired protein and a VSV-G expression plasmid are co-introduced into packaging cells having the gag and pol genes, and the culture supernatant is used as a virus-containing fluid. Alternatively and desirably, a VSV-G expression plasmid is introduced into packaging cells infected with the above virus-containing fluid, and the culture supernatant is used as a virus-containing fluid. The virus-containing fluid is preferably concentrated according to need. The method of preparing a replication defective retrovirus vector is not limited to such method, however.

The titer of the replication defective retrovirus vector in the virus-containing fluid mentioned above is preferably $1\times10^8$ to $1\times10^{14}$ cfu/ml, more preferably $1\times10^9$ to $1\times10^{14}$ cfu/ml.

The titer of the virus-containing fluid is defined as the number of infected cells after addition of the virus-containing fluid to NIH3T3 cells (American Type Culture Collection CRL-1658). More specifically, 1 ml of a virus solution diluted at a dilution ratio of $10^2$ to $10^6$ is added to $5\times10^4$ NIH3T3 cells occurring in each well (base area about 9.4 cm$^2$) of each 6-well culture plate, and the proportion of cells expressing the neomycin resistance gene as a marker is determined based on the resistance to G418 (neomycin). The titer of the virus-containing fluid is calculated from the data thus obtained.

How to infect avian embryos with a replication defective retrovirus vector is now described.

The transgenic birds according to the present invention can be adequately obtained by the method which comprises infecting avian embryos with the replication defective retrovirus vector containing a foreign gene and allowing the embryos to hatch.

An embryo is a young animal at the early stage of development of a multicellular animal, is enveloped in a chorion or eggshell or is in the mother's body and does not yet take food independently. Hatching means coming out of the chorion or eggshell and beginning to take food independently.

The embryo is desirably infected with the replication defective retrovirus vector at least 24 hours after the start of incubation. More desired is an embryo not earlier than 32 hours but not later than 72 hours after the start of incubation. Still more desired is an embryo not earlier than 48 hours but not later than 64 hours of incubation. Preferred as the site of infection, namely the site of introduction of the virus-containing fluid, is the inside of the heart or blood vessel formed in the embryo. For the purpose of producing G0 transgenic chimeric avians with high gene transfer efficiency, it is preferable that the gene transfer be carried out at the early stage at which the cardiac pulsation can be observed (within 6 hours after the start of cardiac pulsation). This is concluded from the viewpoint that the gene is to be distributed to the whole body by means of blood circulation and from the viewpoint that the number of cells is small.

Incubation means that fertilized avian eggs just after egg laying or stored, immediately following egg laying, in an environment in which development thereof is impossible are maintained in an environment in which development thereof is possible. In the case of chickens, for instance, an optimum environment for development is such that the incubation temperature is optimally 37.2 to 37.8° C. in a three-dimensional incubator (38.9 to 39.4° C. at the upper end of a planar incubator or the like) and the humidity is optimally about 40 to 70%. The environment to be employed is not limited to such an environment, however. On the occasion of incubation, eggs are turned. The egg turning is preferably carried out at an angle of at least 30° at least twice a day. The conditions are not restricted to these, however.

Microinjection is a method of introducing a virus-containing fluid directly into a specific site using a tapered glass microtube under a microscope. In this study, the virus-containing fluid is introduced into such a specific site as the heart or blood vessel and, therefore, the technique of microinjection is preferred to other methods of gene transfer, for example the lipofection and electroporation techniques.

The bird to be used in the practice of the invention is not particularly restricted but preferably is a poultry bird utilizable as a farm animal. As the poultry bird, there may be mentioned chickens, turkeys, ducks, ostriches, quails and domestic ducks, among others. Among them, chickens are particularly preferred since they are readily available and are fecund as egg-laying species, eggs thereof are large, and the technique of mass rearing has been established.

G0 transgenic chimeric birds can be obtained by infecting avian embryos with a replication defective retrovirus vector containing a foreign gene and allowing the embryos to hatch, as mentioned above.

When G0 transgenic chimeric birds having a foreign gene in germ cells thereof are mated with wild-type birds, G0 transgenic chimeric birds or descendants thereof and, after hatching, nestlings are screened, G1 transgenic birds can be obtained. In G0 transgenic chimeric birds, the probability of introduction of the foreign gene into all cells is low and, in most cases, they are in a chimeric state in which there coexist cells different in genotype, namely cells resulting from foreign gene transfer and wild type cells. On the other hand, G1 transgenic birds have the transferred gene uniformly in all somatic cells. The gene transfer into somatic cells or germ cells can be confirmed by examining DNAs and RNAs derived from blood, somatic cells, spermatozoa and eggs by the technique of PCR etc. and can also be confirmed based on the expression of the desired protein. The expression of the desired protein can be checked by the ELISA method, the electrophoretic method and/or the activity measurement of the desired protein, for instance.

G2 and the subsequent generations of transgenic birds can be produced by mating G1 transgenic birds. Conceivable as the mating types are G1 transgenic males and wild type females, G1 transgenic females and wild type males, G1 transgenic males and females, for instance. Further, back crossing of descendants thereof with parents thereof is also possible. Among them, the mating type involving G1 males and wild type females is preferred from the efficiency viewpoint since one G1 male can be mated with a plurality of wild type females.

The method of producing a target protein according to the invention is characterized in that the target protein is recovered from the above-mentioned transgenic birds. More particularly, the method is characterized in that the desired protein is recovered from the blood of the transgenic birds produced, somatic cells thereof and/or eggs thereof by one or a combination of extraction, purification and activation. The methods to be used for extraction and purification are not particularly restricted but include, among others, methods comprising one and/or a combination of fractional precipitation, centrifugation, separation into two phases, ultrafiltration, membrane separation, chromatography, immunochemical methods and crystallization.

The feline-derived protein produced in the transgenic birds according to the invention amounts to about 24 μg/ml in serum or about 420 μg/ml in egg white, as shown in the example section given later herein. In the case of the human-derived erythropoietin-producing transgenic birds disclosed in United States Patent Application Publications 2004/0019922 and 2004/0019923, the erythropoietin production is about 10 μg/ml. Therefore, the transgenic birds according to the present invention can produce the desired protein at higher concentration levels.

The present invention also relates to a polyethylene glycol (PEG)-modified feline-derived protein obtainable by chemical modification, with PEG, of the feline-derived protein produced in the manner mentioned above. As the feline-derived protein, there may be mentioned the same ones as those mentioned above.

The feline-derived protein is preferably purified prior to addition of PEG. The feline-derived protein can be purified from a solution prepared from transgenic avian eggs, in particular the egg white component, by dilution with pure water or equilibrated salt solution by a column technique or filtration. The dilution is carried out for the purpose of reducing the viscosity of egg white and carrying out the column technique smoothly. While a high dilution ratio is desired for the viscosity reduction, the increase in volume makes the recovery difficult; therefore, the dilution ratio is preferably 2 to 10 times, more preferably 5 to 6 times.

The method of recovering the desired feline-derived protein from the egg white solution includes, but is not limited to, such purification methods as salting out, adsorption column chromatography, ion exchange column chromatography, gel filtration column chromatography and antibody column technique, employed either singly or in combination. The adsorption column chromatography includes Blue Sepharose chromatography and heparin chromatography, among others, and the ion exchange column chromatography is, for example, anion exchange chromatography.

While it is reported that when the hematopoietic effect of the erythropoietin was checked in such rodents as mice and rats, the increase in the number of reticulocytes was maximum after 4 days following single administration into blood and no more effect was observed on the 7th day, it is known that the addition of polyethylene glycol (PEG), which is a long-chain molecule, results in inhibition of metabolism in the liver, prolongation of the life in blood and prolongation of the drug efficacy period and, in a hematopoietic experiment in rats, the effect lasts for 14 days, namely twice the duration mentioned above. An N-hydroxysuccinimidyl active ester derivative of PEG can be bound to a lysine residue and the N terminus of the protein molecule. The present invention is characterized by, but is not limited to, the addition of PEG to feline-derived erythropoietin for prolonging the life thereof in blood.

With the increase in molecular weight of PEG added, the life of the PEG-EPO complex in blood is prolonged. However, the addition of very high molecular PEG inhibits the hematopoietic effect of EPO (WO 02/032957), so that the weight average molecular weight of PEG is preferably 5 to 40 kDa so that the in vivo hematopoietic effect may be maximized, more preferably 10 to 30 kDa, and still more preferably 20 kDa. The weight average molecular weight of PEG is the value determined by MALDI-TOF mass spectrometry.

Feline-derived erythropoietin has at least three sites where PEG can bind thereto and, therefore, 1 (mono), 2 (di) or 3

(tri) PEG molecules can bind to one protein molecule. Since, however, PEG molecules bound to a plurality of sites inhibit the receptor binding ability of EPO, leading to decreases in in vivo activity, the mono-substituted form is preferred.

The PEG-modified feline-derived protein according to the invention is preferably one in which the number of PEG molecules added is 1 or 2 or more and which has an apparent molecular weight, per PEG-modified molecule, of from 100 kDa to 900 kDa as determined by gel filtration column chromatography in an aqueous solvent, more preferably one in which the number of PEG molecules added is 1 and which has an apparent molecular weight of from 100 kDa to 500 kDa as determined in the above manner.

In the present specification, the above-mentioned apparent molecular weight determination by gel filtration column chromatography is carried out using the low-pressure chromatograph AKTA explorer 100 (product of Amersham) and the gel filtration column Superdex 200 10/300 (product of Amersham).

The present invention further relates to a PEG-modified feline-derived protein composition.

The PEG-modified feline-derived protein composition according to the invention comprises a mixture of a PEG-modified feline-derived protein in which the number of PEG molecules added is 1 or 2 or more and which has an apparent molecular weight, per PEG-modified molecule, of from 100 kDa to 900 kDa, a PEG-modified feline-derived protein in which the number of PEG molecules added is 1 and which has an apparent molecular weight, per PEG-modified molecule, of from 100 kDa to 500 kDa and/or the non-PEG-modified feline-derived protein as obtained by the production method mentioned above and contains at least one PEG-modified feline-derived protein.

The invention further relates to a medicinal composition for feline use which comprises, as an active ingredient, the above-mentioned PEG-modified feline-derived protein or PEG-modified feline-derived protein composition.

The medicinal composition for feline use according to the invention has feline erythropoietin activity and prolonged drug activity and therefore can be suitably used in the treatment of feline renal anemia.

The medicinal composition for feline use according to the invention can be administered parenterally. As the route of parenteral administration, there may be mentioned intravenous injection, intravenous drip infusion, hypodermal injection, transmucosal administration (e.g. transpulmonary, transnasal, etc.) and transdermal administration.

The dose of the medicinal composition for feline use according to the invention is not particularly restricted and cannot be specified without reservation, either, in view of the differences in responsiveness to erythropoietin in individual diseased animals. Generally, however, it may be administered intravenously, for example, twice a week at a dose of about 0.5 to 50 µg per feline as expressed in terms of the weight of the PEG-modified feline-derived protein.

The present invention further relates to a method of producing a PEG-modified feline-derived protein composition which comprises causing a succinimidyl ester derivative of PEG to add to the above-mentioned feline-derived protein.

The succinimidyl ester derivative of PEG is not particularly restricted but includes, among others, the succinimidylpropionate ester and succinimidyl-alpha-methylbutanoate ester.

The mole ratio between the succinimidyl ester derivative of PEG to be added and the feline-derived protein is preferably 1:1 to 1:10 as expressed in terms of (feline-derived protein):(succinimidyl ester derivative of PEG).

The reaction temperature and reaction time are not particularly restricted but preferably are 4 to 37° C. and 0.5 to 2 hours, respectively.

EFFECT OF THE INVENTION

According to the present invention, transgenic birds capable of producing a feline-derived protein and a method of production thereof are provided. As a result, transgenic birds producing a feline-derived cytokine and a method of production thereof are provided. Furthermore, transgenic birds producing a feline-derived erythropoietin and a method of production thereof are provided. Transgenic birds producing erythropoietin at higher concentrations than in the prior art and the production thereof have become possible.

BEST MODES FOR CARRYING OUT THE INVENTION

The following examples illustrate the present invention in detail. These examples are, however, by no means limitative of the scope of the present invention. Unless otherwise specifically described, gene manipulation procedures were carried out according to the typical methods (J. Sambrook, E. F. Fritsch, T. Maniatis; Molecular Cloning, A Laboratory Manual, 2nd Ed., Cold Spring Harbor Laboratory). Unless otherwise specifically described, cell cultures were carried out according to the typical methods (KOYAMA, Hideki (ed.): "Saibo-Baiyo Labo Manual (Cell Culture Labo Manual)", Springer Verlag Tokyo, 1st Ed.). When trademarks are given, the instructions given in the manuals attached were followed, unless otherwise specifically described.

Example 1

Construction of Feline-derived Erythropoietin Gene Expression Plasmid pMSCVneobactfEPO pMSCVneobact (SEQ ID NO:2) was totally synthesized based on the relevant prior art document (Gene Ther. 1994, March: 1(2):136-8) and internet information (http://www.ncbi.nlm.NIH.gov/etc.) and inserted into pUC19 (GenBank Accession No. X02514) at a site between EheI (235) and PvuII (628) (products of Toyobo). The product was cleaved with HindIII (product of Takara Bio) and, after treatment with Alkaline Phosphatase BAP (product of Takara Bio), the desired fragment was purified and recovered using MinElute Reaction Cleanup Kit (product of QIAGEN). This was electrophoresed on 1% agarose and the desired fragment was purified and recovered using MinElute Gel Extraction Kit (product of QIAGEN) (Example 1 vector fragment).

pUCfEPO (SEQ ID NO:3) encodes, at 911 to 1489 bp, the feline-derived erythropoietin sequence. A fragment amplified by PCR using Pyrobest DNA polymerase (product of Takara Bio) as the DNA polymerase and pUCfEPO as the template, together with two chemically synthesized oligonucleotides 5'-agcc aagcttaccatggggtcgtgcgaatgtcctgccctgctgcttc-3' (SEQ ID NO:4) and 5'-cgataagcttacgcgttcacctgtctcctcttcggcag-3' (SEQ ID NO:5) (each underlined portion being a HindIII restriction enzyme site) as primers was purified and recovered using MinElute PCR Purification Kit (product of QIAGEN) and cleaved with HindIII (product of Takara Bio). This was subjected to 1% agarose gel electrophoresis and the desired fragment was purified and recovered using MinElute Gel Extraction Kit (product of QIAGEN) (Example 1 insert fragment).

Example 1 vector fragment and Example 1 insert fragment were joined together using DNA Ligation Kit Ver. 2.1 (product of Takara Bio) and the ligation product was used to transform *E. coli* DH5alpha Competent Cells (product of Takara Bio). From among transformant stains obtained, a plasmid having the structure shown in FIG. 1 was selected and named pMSCVneobactfEPO.

The marker gene beta-lactamase gene, the virus packaging signal sequence phi+, the marker gene neomycin resistance gene, the non-tissue-specific promoter gene beta-actin promoter and the long repeat 5LTR and 3LTR, shown in FIG. 1, are all derived from pMSCVneobact.

Example 2

Retrovirus Vector Preparation Using pMSCVneobactfEPO and pVSV-G

Hereinafter, unless otherwise specified, the medium used was Dulbecco's Modified Eagle Medium (DMEM) (product of Gibco) containing 10% of fetal bovine serum (FBS) and 50 units/ml each of penicillin and streptomycin. The cultivation was carried out at 37° C. in the presence of 5% $CO_2$. The plasmid DNA used in the retrovirus vector was Endo Free Plasmid Maxi Kit (product of QIAGEN).

For retrovirus vector preparation from the plasmid pMSCVneobactfEPO constructed in Example 1, a collagen-coated culture dish having a diameter of 100 mm was sowed with GP293 packaging cells having the gag and pol genes ($5\times10^6$ cells/dish; 70% confluent) (90% confluent on the next day). On the next day, the medium was removed, and 7.2 ml of the medium and 10 µl of 25 mM chloroquine (product of Sigma) were added, followed by further 1 hour of cultivation. A 56-µl portion of Lipofectamine 2000 (product of Invitrogen) was suspended in 1.4 ml of Opti-MEMI medium (product of Gibco), and the suspension was allowed to stand at room temperature for 5 minutes. A 12-µg portion of pMSCVneobactfEPO and 12 µg of pVSV-G were suspended in 1.4 ml of Opti-MEMI medium. The Lipofectamine 2000 solution and plasmid DNA solution were mixed up and the mixture was allowed to stand at room temperature for 20 minutes. The whole amount of this was added to the culture dish and cultivation was carried out for 6 hours. After 6 hours, the medium was removed, 9 ml of the medium and 200 µl of 1 M HEPES Buffer Solution (product of Gibco) were added, and cultivation was further carried out for 24 hours.

The culture supernatant was collected in a centrifuge tube through a 0.45-µm cellulose acetate filter (product of Advantec). The filtrate was centrifuged at 28,000 rpm (50,000×g) for 1.5 hours using the ultracentrifuge CS100GXL (product of Hitachi Koki). The supernatant was removed, 20 µl of TNE buffer (50 mM Tris-HCl (pH 7.8), 130 mM NaCl, 1 mM EDTA) was added to the sediment, the mixture was allowed to stand at 4° C. overnight and, after thorough suspending, centrifuged at 12,000 rpm for 1 minute using a small-sized high-speed centrifuge, and the supernatant was passed through a 0.45-µm Durapore Ultra-Free filter (product of Advantec) to give a virus-containing solution.

Example 3

Virus Titer Measurement

The virus titer is defined as the number of infected cells after addition of the virus-containing fluid to NIH3T3 cells (American Type Culture Collection CRL-1658). A 1-ml portion of the virus solution of Example 2 as diluted at a dilution ratio of $10^2$ to $10^6$ was added to $5\times10^4$ NIH3T3 cells contained in each well (base area about 9.4 $cm^2$) of each 6-well culture plate, and the proportion of cells expressing the neomycin resistance gene as a marker was determined based on the resistance to G418. If 4 colonies appear at a dilution ratio of $10^6$, the virus titer will be $4\times10^6$ cfu/ml.

More specifically, 6-well culture plates were sowed with $5\times10^4$ NIH3T3 cells per well on the day before the start of titer measurement, and the cells were cultured. On the next day, the cell culture medium was replaced with 900 µl of the medium containing 9 µg/ml of polybrene, the virus-containing fluid was diluted to $10^{-1}$ to $10^{-5}$ with the medium and 100-µl portions of each dilution was added to each well for infection (final polybrene concentration being 8 µl/ml). After 4 to 6 hours of cultivation, 1 ml of the medium was further added to each well. On the next day, the medium was replaced with the medium containing 800 µg/ml of G418 and, thereafter, the G418-containing medium was exchanged for the old medium at 3- to 4-day intervals. About 2 weeks after infection, the plates were stained with a methylene blue solution, the colonies obtained were counted, and the titer was determined. The measurement results are shown in Table 1.

Example 4

Selection of Feline-derived Erythropoietin Stable Packaging Cells

On the day before viral infection, 24-well culture plates were sowed with $1.5\times10^4$ GP293 cells per well, and the cells were cultured. On the day of viral infection, 1 ml of the medium containing 10 µg/ml of polybrene was exchanged for the medium, followed by infection with the virus-containing fluid prepared in (Example 2). Thereafter, cells were cloned by the limiting dilution method. More specifically, on the next day, cells were suspended in the medium containing 800 µg/ml of G418 and the suspension was diluted with the same medium to a content of 10 cells/ml. The cell dilution was distributed in 100-µl portions into the wells of 96-well culture plates (so that one cell might be contained in each well). A cell line showing a high cell growth rate and morphologically close to GP293 was selected and, thus, a feline-derived erythropoietin stable packaging cell clone was obtained.

Example 5

Retrovirus Vector Preparation Using Feline-derived Erythropoietin Stable Packaging Cells and pVSV-G A collagen-coated culture dish having a diameter of 100 mm was sowed with the feline-derived erythropoietin stable packaging cells obtained in Example 4 ($5\times10^6$ cells; 70% confluent)(90% confluent on the next day). On the next day, the medium was removed, and 7.2 ml of the medium and 10 µl of 25 mM chloroquine were added, followed by further 1 hour of cultivation. A 56-µl portion of Lipofectamine 2000 was suspended in 1.4 ml of Opti-MEMI medium, and the suspension was allowed to stand at room temperature for 5 minutes. pVSV-G (12 µg) was suspended in 1.4 ml of Opti-MEMI medium. The Lipofectamine 2000 solution and plasmid DNA solution were mixed up, and the mixture was allowed to stand at room temperature for 20 minutes. This was added to the culture dish, followed by 6 hours of cultivation. The medium was removed, 9 ml of the medium and 200 µl of 1 M HEPES Buffer Solution were added, and the cultivation was continued for 24 hours. The culture supernatant was passed through a 0.45-μm cellulose acetate filter and collected in a centrifuge tube. The filtrate was centrifuged at 28,000 rpm (50,000×g) for 1.5 hours using an ultracentrifuge. The supernatant was removed, 20 μl of TNE buffer solution was added to the sediment, the mixture was allowed to stand at 4° C. overnight and, after thorough suspending, centrifuged at 12,000 rpm for 1 minute using a small-sized high-speed centrifuge, and the supernatant was passed through a 0.45-μm Durapore Ultra-Free filter to give a virus-containing fluid. Thus, a virus-containing fluid having a titer of $10^8$ cfu/ml or higher was obtained.

Example 6

Construction of Wpre Sequence-containing Feline-derived Erythropoietin Gene Expression Plasmid Pmscvneobactfepowpre and Preparation of Retrovirus Vector pMSCVneobactfEPO was cleaved with ClaI (product of Takara Bio) and, after BAP treatment, purified and recovered. The purification and recovery were carried out using the product described in (Example 1). This was subjected to 1% agarose gel electrophoresis, and the desired fragment was purified and recovered (Example 6 vector fragment). A fragment amplified from WPRE sequence-containing pWHV8 (American Type Culture Collection 45097) by PCR using, as primers, two chemically synthesized oligonucleotides 5'-cc<u>atcgat</u>aatcaacctctggattacaaaatttgtga-3' (SEQ ID NO:6) and 5'-cc<u>atcgat</u>caggcggggaggcg-3' (SEQ ID NO:7) (each underlined portion being a ClaI restriction enzyme site) was purified, recovered and cleaved with ClaI. This was subjected to 1% agarose gel electrophoresis, and the desired fragment was purified and recovered (Example 6 insert fragment).

Example 6 vector fragment and Example 6 insert fragment were joined together and the ligation product was used to infect *E. coli* DH5alpha. From among the transformant strains obtained, a plasmid having structure shown in FIG. 2 was selected and named pMSCVneobactfEPOwpre. Stable packaging cells and retrovirus vectors can be prepared in the same manner as in the examples mentioned above. The use of the WPRE sequence makes it easy to obtain high-titer stable packaging cells. This is presumably due to enhancement of the transcriptional activity or stabilization of the RNA by the use of the WPRE sequence.

Example 7

Microinjection of Retrovirus Vector into Chicken Embryos and Artificial Hatching Microinjection and artificial hatching were carried out under sterile conditions. Fertilized chicken eggs (Shiroyama Shukeijo (Shiroyama Chicken Farm)) were externally disinfected with a disinfectant (product of Showa Furanki) and ethanol. An incubator model P-008(B) (product of Showa Furanki) was adjusted to an environment of 38° C. and 50 to 60% humidity, and incubation was carried out from the start of power supply (0 hour) while thereafter turning eggs at 90° at 15-minute intervals.

After the lapse of about 55 hours from the start of incubation, eggs were taken out of the incubator, a circular portion with a diameter of 3.5 cm was cut off from the sharper end of each egg using a minirouter (product of Proxxon) equipped with a diamond edge (edge diameter 20 mm, shaft diameter 2.35 mm). A circular portion with a diameter of 4.5 cm was cut off from the sharper end of each double-yolked egg (Shiroyama Shukeijo), the contents were discarded, the contents of each fertilized egg were transferred to the remaining eggshell, and the embryo was shifted upwards by means of the inner cylinder of a syringe. Under the stereoscopic microscope system SZX12 (product of Olympus), the virus-containing fluid was poured into FemtoChip II (product of Eppendorf) and about 2 μl of the virus solution of Example 5 or 6 was microinjected into the embryo using FemtoJet (product of Eppendorf).

The circular hole was covered with Saran Wrap (product of Asahi Chemical Industry) cut to a size of about 8×8 cm², using egg white as an adhesive, and the egg was returned to the incubator for continued incubation. The mode of egg turning was changed to 30° turning at 30-minute intervals. On the 20th day after the start of incubation, about 20 holes were bored in the Saran Wrap using a 20 G syringe needle, and oxygen was fed to the incubator at a rate of 60 cc/min for hatching. When the chick began pecking, the eggshell was broken to allow hatching. The hatchability data in this artificial hatching are shown in Table 1.

TABLE 1

|  | Virus titer (cfu/ml) | Number of eggs | Number of hatchlings | Hatchability (%) |
|---|---|---|---|---|
| 1st | $1.7 \times 10^8$ | 20 | 1 | 5 |
| 2nd | $1.4 \times 10^8$ | 22 | 0 | 0 |
| 3rd | $7.3 \times 10^6$ | 22 | 0 | 0 |
| 4th | $1.7 \times 10^8$ | 21 | 1 | 5 |
| 5th | $6.8 \times 10^7$ | 18 | 6 | 33 |
| 6th | $5.0 \times 10^7$ | 17 | 7 | 41 |
| 7th | $5.7 \times 10^6$ | 16 | 5 | 31 |
| 8th | $1.9 \times 10^8$ | 15 | 2 | 13 |
| 9th | $2.7 \times 10^8$ | 11 | 2 | 18 |
| 10th | $8.7 \times 10^8$ | 25 | 2 | 8 |
| 11th | $7.8 \times 10^8$ | 43 | 7 | 16 |
| 12th | $3.8 \times 10^8$ | 20 | 3 | 15 |
| Total |  | 250 | 36 | 14 |

Example 8

Confirmation of Expression in Blood and Eggs of Feline-derived Erythropoietin Expression Transgenic Chickens The nestlings born in (Example 7) were fed for growth. The feeds used were SX Safety and Neo-Safety 17 (products of Toyohashi Shiryo (Toyohashi Feedstuff)) for young chicks. Blood was collected from the transgenic chickens via the vein under the wing. The blood collected was placed in an Eppendorf tube and, after at least 30 minutes of standing at room temperature, centrifuged at 3,000 rpm at 4° C. for 5 minutes using a small-sized high-speed centrifuge to completely separate into serum and blood clot. The supernatant was employed as serum. On the occasion of extraction from eggs, egg white and yolk were separated from each other. In extracting from egg yolk, a syringe was inserted into the middle of the egg yolk and the egg yolk was drawn out while preventing the egg white from coming in. The egg white was uniformly homogenized by ultrasonic or physical means. The samples prepared were stored frozen at −80° C. until assaying. For avoiding thawing under freezing, the thawing is preferably carried out rapidly at 37° C.

The feline-derived erythropoietin activity was determined by the cell proliferation assay technique (Japanese Kokai Publication Hei10-94393) using the EPO-dependent cell line BaF/EPOR. In the cell proliferation assay, a working curve for proliferation was constructed using Epogin (product of Chugai Pharmaceutical) as a standard, and the erythropoietin activity of each unknown sample was determined based on the working curve for proliferation. The medium used for BaF/EPOR cells was RPMI 1640 liquid medium (product of Nissui) containing 5% of fetal bovine serum (FBS) and 50 units/ml each of penicillin and streptomycin. In ordinary BaF/EPOR cell cultivation, Epogin was added to a final concentration of 1 U/ml. In cell proliferation assaying, cells at the logarithmic growth phase were used.

In carrying out the cell proliferation assay using BaF/EPOR cells, the Epogin in the medium was first removed. Thus, the cultured BaF/EPOR cells were centrifuged at 1,000 rpm for 5 minutes. The supernatant was removed, and 10 ml of the Epogin-free medium was added to the sediment for suspending the same. The Epogin in the medium was removed by repeating the above procedure three times. Cells were counted and diluted to a concentration of 55,555 cells/ml with the Epogin-free medium. The diluted cell suspension was distributed in 90-µl portions into the wells of 96-well microtiter plates. Thereto were added 10 µl each of Epogin solutions diluted to 25, 16, 10, 6.4, 4.0, 2.5, 1.6 and 1.0 U/ml and the cells were uniformly suspended therein (the final erythropoietin concentrations being 2.5, 1.6, 1.0, 0.64, 0.4, 0.25, 0.16 and 0.1 U/ml, respectively). Each sample to be assayed was diluted serially about 2 to 4 times so that the data might fall within the assay range of the working curve, and 10 µl of each dilution was added to the cells sown for attaining uniform suspension. Three measurements were carried out for each standard sample and each unknown sample. After 2 days of cultivation, 10 µl of the solution included in Cell Counting Kit-8 (product of Dojin Kagaku Kenkyusho (Dojindo Laboratories)) was added to each well. After allowing the color reaction to proceed from 1 to 4 hours, 10 µl of 0.1 mol/l hydrochloric acid was added to terminate the reaction, and the absorbance at 450 nm was measured using a microplate reader. An approximate expression was derived from the measurement results with standard samples by logarithmic approximation, and the activity of each unknown sample was calculated based on the expression obtained.

In the individual showing the maximum expression levels (Individual No. 10-1), the activity in serum was 5,300 IU/ml and that in egg white was 92,000 IU/ml. The expression results in G0 transgenics are shown in FIG. 3. After mastering of the injection technique, the frequency of appearance of G0 transgenics among hatchings was 100%. However, individuals showing high expression levels are ready to die. Since the specific activity of erythropoietin is about 220,000 IU/mg (Eur. J. Biochem. 1990 Dec. 12; 194(2): 457-62) although it may vary depending on the extent of addition of sugar chains, the content in serum can be estimated to be about 24 µg/ml and that in egg white to be about 420 µg/ml based on such data. Due to the difference in amino acid sequence between feline and human erythropoietin species, no correct assays could be made with the Recombigen EPO kit (product of Mitsubishi Kagaku Iatron) using the RIA technique.

Then, the feline-derived erythropoietin levels in blood and in eggs of Individual No. 6-3 were assayed by western blotting. Each sample was electrophoresed under denaturing conditions using 12.5% of e-PAGEL (product of Atto Corp.) and, after transfer to a PVDF membrane, blocking was carried out with PBS containing 10% of skimmed milk and 0.05% of Tween 20, followed by detection with ECL Plus Western Blotting Detection System and Hyperfilm ECL (products of Amersham) using rabbit anti-human EPO antibody (product of G-T Research Products) as the primary antibody and goat anti-rabbit IgG-HRP antibody (product of Zymed Laboratories) as the secondary antibody. The results of the western blotting are shown in FIG. 4.

Example 9

Purification of Feline-derived Erythropoietin from Egg White

The eggs from each individual for which the feline-derived erythropoietin activity had been confirmed in egg white in Example 8 were recovered and feline-derived erythropoietin was recovered and purified from egg white.

Each sample applied to the column was subjected to syringe filtration just prior to using Millex-HV (product of Millipore) with a pore size of 0.45 µm. When the filtration was difficult, the filtration through Millex was carried out after preliminary filtration through Puradix 25 (product of Whatman) with a pore diameter of 2 µm.

During the purification process, the assaying of feline-derived erythropoietin content was carried out using Bicore 3000 (product of BIACORE). An assay chip was prepared by subjecting an anti-human erythropoietin monoclonal antibody (product of R&D Systems) to NHS immobilization to Sensor Chip CM5 research grade (product of BIOCORE) using an amine coupling kit (product of BIOCORE) and, using the same, the concentration was determined using the assaying program attached to the apparatus, with Epogin as a standard substance.

For application to the column, the egg white was subjected to pretreatment for reducing the viscosity. Each refrigerated egg was returned to room temperature and then broken and, after separation into egg yolk and egg white using the eggshell, for instance, the egg white alone was recovered and weighed. The egg white was agitated with a stirrer to entangle the dense egg white, 5 volumes of ultrapure water was added, and the mixture was further stirred. At this point of time, the pH of the egg white had a pH of about 9.0 to 9.3. The pH was adjusted to 5.0 by addition of an appropriate amount of 1 N HCl and, after 15 minutes or longer of stirring, the mixture was centrifuged at 9,500 G at 4° C. for 30 minutes. The supernatant was adjusted to pH 7.0 by addition of 1 M NaOH, and 1 M Tris buffer (pH 7.0) was added to a final concentration of 50 mM. In this step, the maximum recovery of feline-derived erythropoietin was 95%.

Then, Blue Sepharose chromatography was carried out. A 500-ml portion of the egg white solution after pretreatment (egg white of 2 to 3 eggs) was applied to a 50-ml Blue Sepharose 6 Fast Flow column (product of Amersham) equilibrated with 50 mM Tris, pH 7.0. The column was thoroughly washed with 50 mM Tris, pH 7.0 and then eluted with 200 ml of 1 M NaCl, 50 mM Tris, pH 7.0. The eluate fraction was dialyzed overnight against 20 mM MES, pH 6.2 in the conventional manner in a low-temperature room maintained at 4° C. for buffer exchange. In this step, the maximum recovery of feline-derived erythropoietin was 98%.

Then, heparin chromatography was carried out. The Blue Sepharose eluate fraction (after dialysis) was applied in two divided portions to a HiPrep 16/10 Heparin FF column (product of Amersham) equilibrated with 20 mM MES, pH 6.2 and, for each portion, the column was thoroughly washed with 20 mM MES, pH 6.2, and then eluted in a gradient manner while increasing the NaCl concentration to 80 mM. Each time, the column was regenerated with 1 M NaCl and 0.1 M NaOH. The fractions in which feline-derived erythropoietin was confirmed by means of Biacore were recovered. In this step, the maximum recovery of feline-derived erythropoietin was 80%.

Then, buffer exchange was carried out using a desalting column. The Heparin Sepharose eluate fraction was concentrated to a total amount of about 30 to 40 ml by means of Vivaspin 20 (product of Sartorius) with a cutoff molecular weight of 5,000 and applied, in 10-ml divided portions, to a HiPrep 26/10 Desalting column (product of Amersham) equilibrated with 25 mM Tris, pH 7.0, and eluted with the same buffer to recover a protein-containing fraction. This was adjusted to pH 9.0 with 1 M NaOH and further adjusted with 1 M NaCl so that the electric conductivity might amount to 3.0 to 3.2 mS/cm. In this step, the maximum recovery of feline-derived erythropoietin was 95%.

Then, anion exchange column chromatography was carried out. The sample after buffer exchange was applied, in two divided portions, to a 5-ml HiTrap DEAE FF column (product of Amersham) equilibrated with 25 mM Tris (pH 9.0, electric conductivity 3.0 to 3.2 mS/cm) and, for each portion, the pass-through fraction was recovered. The column was regenerated each time with 1 M NaCl. The fractions were concentrated to a total volume of about 2 to 3 ml using Vivaspin 20 with a cutoff molecular weight of 5,000. In this step, the maximum recovery of feline-derived erythropoietin was 92%.

Gel filtration was carried out. The sample after concentration was applied to a Superdex 200 10/300 GL column (product of Amersham) equilibrated with 50 mM borate buffer, pH 9.0 or some other appropriate buffer, followed by elution with the same buffer. Fractions in which the occurrence of feline-derived erythropoietin was confirmed by means of Biacore were recovered and concentrated to a total amount of about 1 to 2 ml using Vivaspin 6 with a cutoff molecular weight of 5,000. In this step, the maximum recovery of feline-derived erythropoietin was 93%.

Each fraction recovered in each purification step was subjected to SDS-PAGE. Each sample was electrophoresed under denaturing conditions using 12.5% e-PAGEL, followed by detection with Bio-Safe Coomassie Stain (product of Bio-Rad). The results of SDS-PAGE for Individual No. 10-1 are shown in FIG. 5.

The protein concentration was determined using DC Protein Assay (product of Bio-Rad) with BSA as a standard. In the individual in which the expression level was maximum (Individual No. 10-1), the purification of egg white gave about 3 mg, per egg white of one egg, of feline-derived erythropoietin.

Example 10

Baf/EPOR Cell Proliferation Assay of Purified Feline Erythropoietin

The feline-derived erythropoietin purified from egg white in Example 9 was subjected to Baf/EPOR cell proliferation assay by the method described in Example 8. As a result, the specific activity was 160,000-290,000 IU/mg.

Example 11

Production of mPEG-modified Feline-derived Erythropoietin

To a solution of feline-derived erythropoietin purified from egg white (dissolved in phosphate or borate buffer with a pH of 8.0 to 9.0) was added methoxyPEG-SPA (succinimidylpropionate ester) or methoxyPEG-SMB (succinimidyl-alpha-methylbutanoate ester) (product of NEKTAR) (the molecular weight of PEG being about 20 kDa), and the resulting mixture was mixed up by inversion at room temperature for 0.5 to 1 hour. A 1/10 volume of 100 mM glycine solution was added and the mixture was mixed up by further inversion at room temperature for 0.5 hour to deactivate the active ester. The solution after reaction was subjected to buffer exchange for 50 mM acetate buffer, pH 4.5, using Prepacked Disposable PD-10 Columns (product of Amersham) or by dialysis, followed by application to a 1-ml HiTrap SP HP column (product of Amersham) equilibrated with the same buffer. The unreacted PEG passed through the column, and mPEG-fEPO and unreacted feline-derived erythropoietin were adsorbed on the column; these were eluted and recovered by eluting with 500 mM NaCl, 25 mM acetate buffer, pH 4.5. The recovered fraction was applied to Superdex 200 10/300 GL equilibrated with 150 mM NaCl+20 mM phosphate buffer, pH 7.5, and fractions corresponding to the number of PEG molecules added of 2 or more, 1 and 0 (unreacted feline-derived erythropoietin) were recovered. The fractions after recovery were properly concentrated by means of Vivaspin 6 with a cutoff molecular weight of 5,000. The activated PEG species, reaction mixture composition, reaction time and mPEG-fEPO products ratio data are summarized in Table 2. For each mPEG-fEPO, the theoretical molecular weight and the molecular weight based on the separation on Superdex 200 10/300 GL are summarized in Table 3. The PEG-modified and gel filtration-purified samples were subjected to SDS-PAGE. The samples were electrophoresed under denaturing conditions using 12.5% e-PAGEL and detected using Bio-Safe Coomassie Stain (product of Bio-Rad). The results of SDS-PAGE are shown in FIG. 6.

TABLE 2

| | | Reaction mixture composition | | | Products ratio (%) | | |
|---|---|---|---|---|---|---|---|
| Activated PEG species | Buffer [1] composition | EPO concentration (mg/ml) | EPO:PEG mole ratio | Reaction time (hr) | di-PEG-fEPO | mono-PEG-fEPO | Unmodified fEPO |
| mPEG-SPA | A | 2.3 | 1:5 | 1.0 | Trace | 29 | 71 |
| | B | 2.3 | 1:5 | 1.0 | Trace | 31 | 69 |
| | A | 2.7 | 1:10 | 0.5 | 6 | 50 | 44 |
| mPEG-SMB | A | 2.3 | 1:5 | 1.0 | 7 | 61 | 32 |
| | B | 2.3 | 1:5 | 1.0 | 11 | 67 | 23 |
| | C | 2.3 | 1:5 | 1.0 | 12 | 67 | 21 |

Note
[1] Buffer composition:
A. 100 mM phosphate buffer, pH 8.0
B. 50 mM borate buffer, pH 8.5
C. 50 mM borate buffer, pH 9.0

TABLE 3

| Molecular weight (in kDa) | fEPO or PEG-fEPO species | | |
|---|---|---|---|
| | di-PEG-SPA(SMB)-EPO | mono-PEG-SPA(SMB)-EPO | Feline-derived erythropoietin (SEQ ID NO: 1) |
| Theoretical molecular weight (excluding sugar chain) | 61 | 41 | 21 |
| Gel filtration molecular weight | 685 | 377 | 41 |

Example 12

Baf/EPOR Cell Proliferation Assay of Mono-PEG-modified Feline-derived Erythropoietin The mono-mPEG-fEPO PEG-modified and purified in Example 11 was subjected to Baf/EPOR cell proliferation assay by the method described in Example 10. The mPEG-fEPO was quantitated as the weight of the protein portion using DC Protein Assay (product of Bio-Rad) with BSA as a standard. As a result, the specific activity was 3,200 to 15,000 IU/mg in the case of mono-mPEG-SPA-fEPO or 4,300 to 8,300 IU/mg in the case of mono-mPEG-SMB-fEPO.

Example 13

Drug Efficacy Duration Measurement of Mono-PEG-modified Feline-derived Erythropoietin Normal Crlj:CD strain male rats (products of Charles River Japan) were subjected to experiment at the age of 7 weeks. Use was made of the mono-mPEG-SPA-fEPO PEG-modified and purified in (Example 11) (specific activity 8,300 IU/mg) was used as a mono-PEG modified feline-derived erythropoietin, non-PEG-modified feline-derived erythropoietin purified from Individual No. 10-1 in Example 9 (specific activity 160,000 IU/mg) as a non-PEG-modified feline-derived erythropoietin, and Epogin (specific activity 180,000 IU/mg; value described in Interview Form) as CHO-produced human erythropoietin. These were diluted with physiological saline containing 0.05% of human serum albumin and 0.05% of Tween 20 and administered at a single dose of 2 ml/kg. Rats were divided into 12 groups each consisting of 5 rats, and two groups each were administered with the mono-mPEG-SPA-fEPO diluted to 25, 5, or 1 µg/ml µg (the dose being 50, 10 or 2 µg/kg, respectively) or the non-PEG-modified feline-derived erythropoietin or Epogin each diluted to 25 µg/ml (the dose being 50 µg/kg). The control groups were administered with the solvent alone. The test substances were prepared in advance and frozen stored at −20° C. Just before administration, they were thawed at room temperature and administered into the caudal vein at about the body temperature using a 27 G injection needle. For lessening the burden on test animals, blood sampling was carried out alternately in the two groups given the same dose of the same test substance (group A and group B, respectively) as follows: group A: 0, 4, 10, and 21 days after administration of the test substance; group B: 2, 7 and 15 days after administration of the test substance. Without anesthetizing, 0.5-ml blood samples were collected from the common carotid artery using a 23 G injection needle. For each sample, reticulocytes were counted using the automated reticulocyte measuring apparatus R-3000 (product of Sysmex).

The significances of the differences between the mean reticulocyte count values in the control group and in the mono-mPEG-SPA-fEPO group, non-PEG-modified feline-derived erythropoietin group and Epogin group at each point of measurement were tested by the Dunnett's multiple comparison method using the SAS system (product of SAS Institute). The significance levels were 5% on both sides.

The measurement results are shown in FIG. 7. In the Epogin (50 µg/kg) group and mono-mPEG-SPA-fEPO groups (50 µg/kg and 10 µg/kg), the reticulocyte count significantly dropped on the day 2 after administration as compared with the control group and, on the 4th day, it increased to show the maximum value. On the 7th day after administration, it again dropped to a level below the level of the control group. In the mono-mPEG-SPA-fEPO (2 µg/kg) group and non-PEG-modified feline-derived EPO (50 rig/kg) group, no significant increases in reticulocyte count were observed. In the mono-mPEG-SPA-EPO group, the in vivo reticulocyte activity was high in spite of the decreased specific Baf/EPOR cell proliferating activity as compared with the non-PEG-modified feline-derived EPO. Presumably, this was due to an improvement in in vivo stability of erythropoietin as brought about by modification with PEG.

SEQUENCE LISTING

Figure 1:
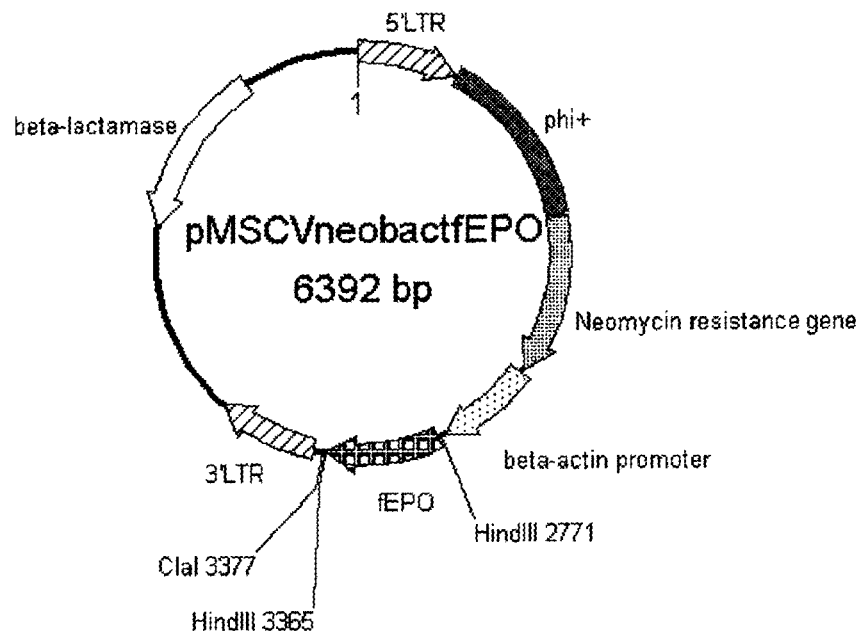
FIG. 1 The figure shows the structure of the feline-derived erythropoietin expression vector pMSCVneobactfEPO constructed in Example 1. The symbol phi+ indicates the virus packaging signal sequence. The packaging signal sequence of Moloney murine leukemia virus is accompanied by a part of gag with TAG substituting for the initiation codon (ATG) in gag. fEPO indicates the feline-derived erythropoietin gene. 5'LTR and 3'LTR indicate the LTR sequences of MSCV.
Figure 2:
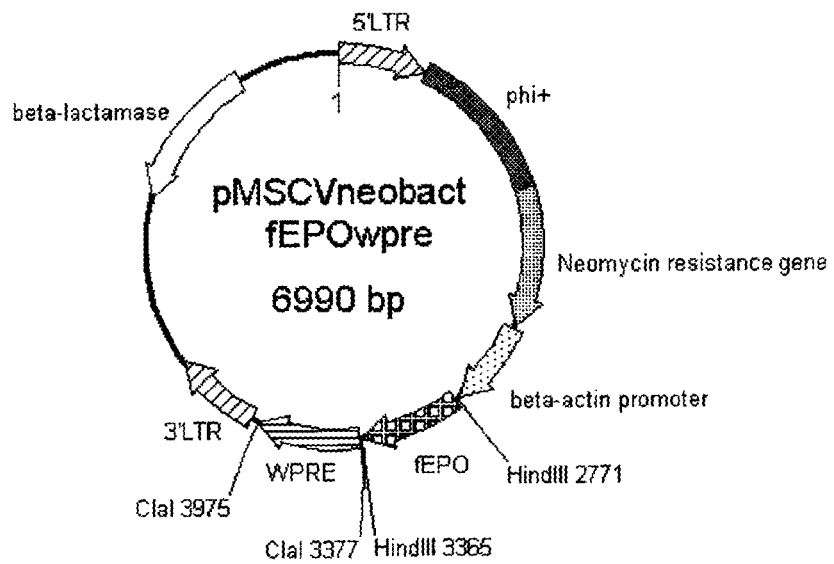
FIG. 2 The figure shows the structure of the feline-derived erythropoietin expression vector pMSCVneobactfEPOwpre constructed in Example 6. The symbol phi+ indicates the virus packaging signal sequence. The packaging signal sequence of Moloney murine leukemia virus is accompanied by a part of gag with TAG substituting for the initiation codon (ATG) in gag. fEPO indicates the feline-derived erythropoietin gene. 5'LTR and 3'LTR indicate the LTR sequences of MSCV. WPRE indicates the woodchuck hepatitis virus-derived posttranscriptional regulatory factor.
Figure 3:
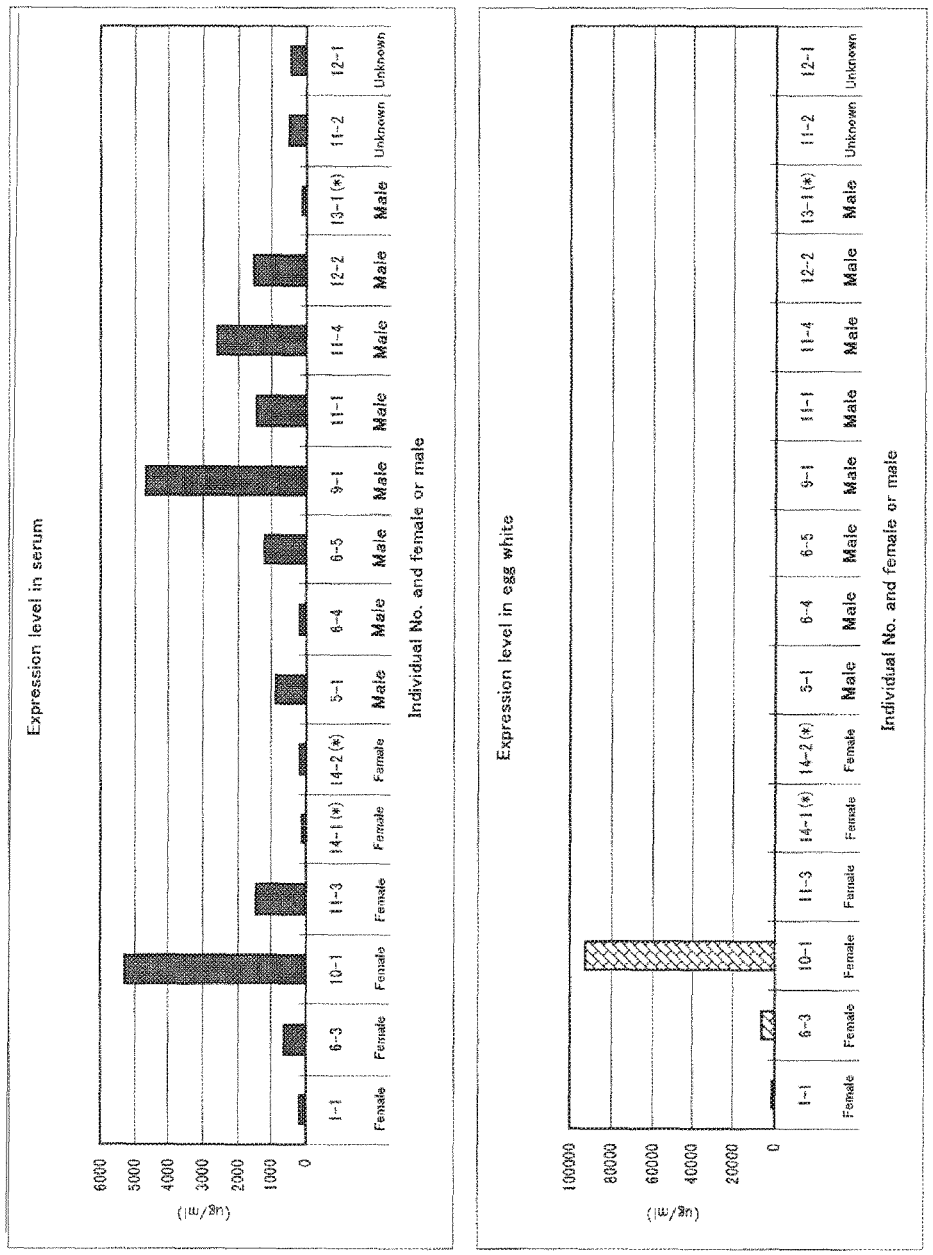
FIG. 3 The figure shows the activities in serum and egg white of transgenic chickens as measured in Example 8. The activities were measured by cell proliferation assaying using BaF/EPOR, which is an EPO-dependent cell line, with Epogin as standard erythropoietin. "Sex unknown" means that the relevant individual was sacrificed before sex judgment. Chickens marked with (*) were transgenic chickens produced by using the pMSCVneobactfEPO vector, and others were transgenic chickens produced by using pMSCV-neobactfEPOwpre. In the individual showing maximum expression levels (Individual No. 10-1), the activity in serum was 5, 300 IU/ml and that in egg white was 92,000 IU/ml.
Figure 4:
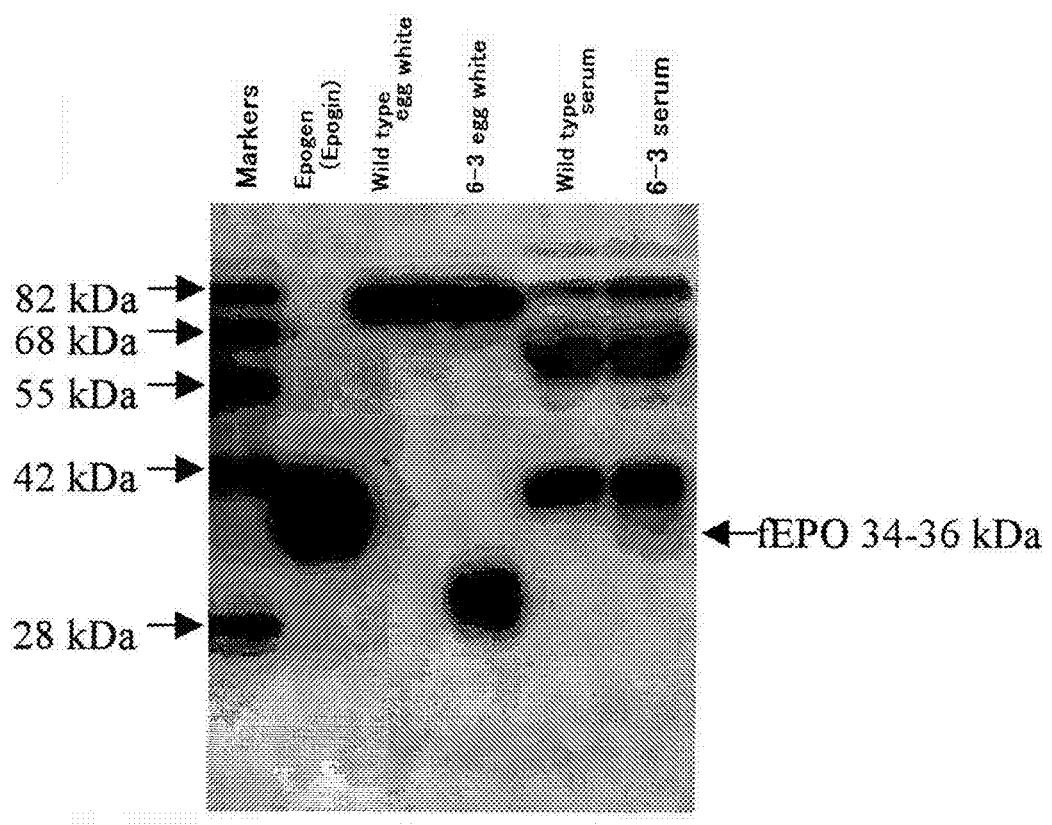
FIG. 4 The figure shows the results of western blot analysis of the serum and egg white of a transgenic chicken (Individual No. 6-3) as carried out in Example 8 using anti-feline-derived erythropoietin antibody. The expression level in serum in the individual No. 6-3 was 620 IU/ml and that in egg white was 6,400 IU/ml. The markers used were molecular weight markers (Dr. Western markers; product of Oriental Yeast). The molecular weight of erythropoietin is about 32 to 34 kDa. Epogin was used as a reference sample. Wild-type samples were derived from a non-transgenic chicken. Epogin was electrophoresed in an amount of 1.2 U/lane, and the egg white and serum were electrophoresed in amounts of 0.2 μl/lane and 0.4 μl/lane, respectively. The bands given by the wild type are bands nonspecific to erythropoietin. As compared with the wild type, a band due to serum-derived erythropoietin can be confirmed at the same position as that of Epogin, although in a slight amount. Egg white-derived erythropoietin shows a migration distance corresponding to a lower molecular weight as compared with the ordinary species. This is presumably due to the difference in sugar chain modification pattern.
Figure 5:
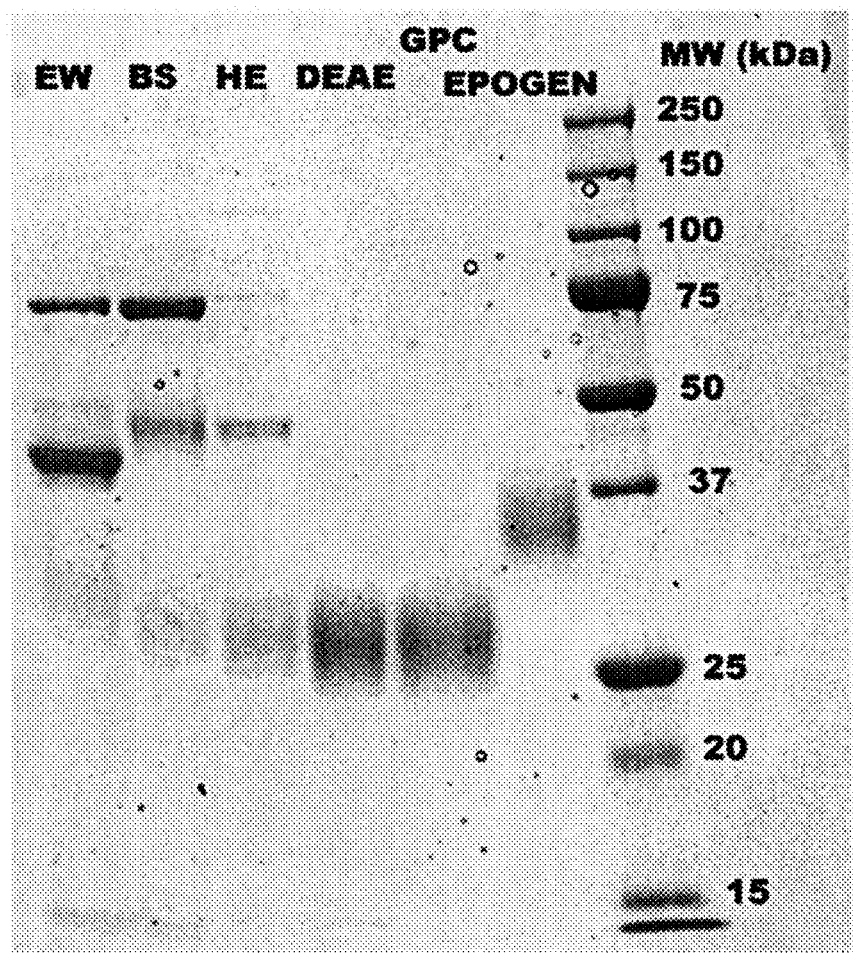
FIG. 5 The figure shows the results of SDS-PAGE in each step of purification of feline-derived erythropoietin in the egg white from a transgenic chicken (Individual No. 10-1) as carried out in Example 9. The sample size was 2 μg/lane (except for Epogin: 10 μl/lane). From the left, there are shown the egg white (EW), Blue Sepharose chromatography eluate fraction (BS), heparin chromatography eluate fraction (HE), anion exchange column chromatography through-out fraction (DEAE), gel filtration column chromatography eluate fraction (GPC), and Epogin (Epogen). Used as the molecular weight markers were Precision Plus Protein Standards Dual Color (product of Bio-Rad). In agreement with the results of western blot analysis as shown in FIG. 4, a band due to feline-derived erythropoietin purified from egg white can be confirmed at a position corresponding to a lower molecular weight as compared with Epogin.
Figure 6:
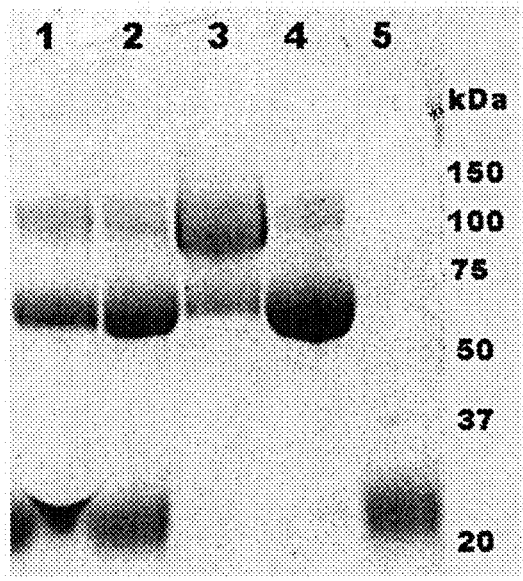
FIG. 6 The figure shows the results of SDS-PAGE of the reaction mixture resulting from modification of feline-derived erythropoietin with PEG, and of PEG-fEPO after purification, as performed in Example 11. Each sample was electrophoresed in an amount of 10 μl/lane. Lane 1 shows the results obtained with the PEG modification reaction mixture, Lane 2 with a cation exchanger-bound fraction, Lane 3 with di-mPEG-SPA-fEPO, Lane 4 with mono-mPEG-SPA-fEPO, and Lane 5 with unmodified fEPO. In Lane 1, there is a band unstainable with CBB around 30 to 40 kDa; this probably corresponds to the unreacted PEG. This band was eliminated upon cation exchange chromatography (Lane 2).
Figure 7:
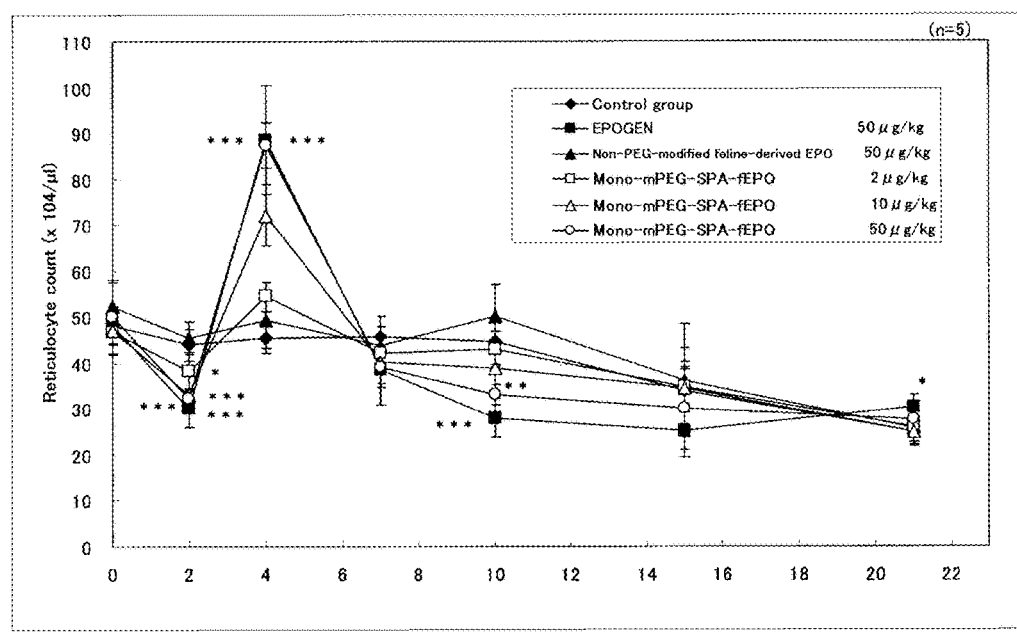
FIG. 7 The figure shows the changes in reticulocyte count in rats following administration of non-PEG-modified feline-derived erythropoietin, mono-mPEG-SPA-fEPO and Epogen as performed in Example 13.

```
<160> NUMBER OF SEQ ID NOS: 7

<210> SEQ ID NO 1
<211> LENGTH: 192
<212> TYPE: PRT
<213> ORGANISM: Felis catus

<400> SEQUENCE: 1

Met Gly Ser Cys Glu Cys Pro Ala Leu Leu Leu Leu Ser Leu Leu
 1               5                  10                  15

Leu Leu Pro Leu Gly Leu Pro Val Leu Gly Ala Pro Pro Arg Leu Ile
                20                  25                  30

Cys Asp Ser Arg Val Leu Glu Arg Tyr Ile Leu Glu Ala Arg Glu Ala
            35                  40                  45

Glu Asn Val Thr Met Gly Cys Ala Glu Gly Cys Ser Phe Ser Glu Asn
        50                  55                  60

Ile Thr Val Pro Asp Thr Lys Val Asn Phe Tyr Thr Trp Lys Arg Met
65                  70                  75                  80

Asp Val Gly Gln Gln Ala Val Glu Val Trp Gln Gly Leu Ala Leu Leu
                85                  90                  95

Ser Glu Ala Ile Leu Arg Gly Gln Ala Leu Leu Ala Asn Ser Ser Gln
            100                 105                 110

Pro Ser Glu Thr Leu Gln Leu His Val Asp Lys Ala Val Ser Ser Leu
        115                 120                 125

Arg Ser Leu Thr Ser Leu Leu Arg Ala Leu Gly Ala Arg Lys Glu Ala
    130                 135                 140

Thr Ser Leu Pro Glu Ala Thr Ser Ala Ala Pro Leu Arg Thr Phe Thr
145                 150                 155                 160

Val Asp Thr Leu Cys Lys Leu Phe Arg Ile Tyr Ser Asn Phe Leu Arg
                165                 170                 175

Gly Lys Leu Thr Leu Tyr Thr Gly Glu Ala Cys Arg Arg Gly Asp Arg
            180                 185                 190

<210> SEQ ID NO 2
<211> LENGTH: 5798
<212> TYPE: DNA
<213> ORGANISM: Artificial
```

<220> FEATURE:
<223> OTHER INFORMATION: Retrovirus vector pMSCVneobact

<400> SEQUENCE: 2

| | | | | | |
|---|---|---|---|---|---|
| aatgaaagac | cccacctgta | ggtttggcaa | gctagcttaa | gtaacgccat | tttgcaaggc | 60 |
| atggaaaata | cataactgag | aatagagaag | ttcagatcaa | ggttaggaac | agagagacag | 120 |
| cagaatatgg | gccaaacagg | atatctgtgg | taagcagttc | ctgccccggc | tcagggccaa | 180 |
| gaacagatgg | tccccagatg | cggtcccgcc | ctcagcagtt | tctagagaac | catcagatgt | 240 |
| ttccagggtg | ccccaaggac | ctgaaatgac | cctgtgcctt | atttgaacta | accaatcagt | 300 |
| tcgcttctcg | cttctgttcg | cgcgcttctg | ctccccgagc | tcaataaaag | agcccacaac | 360 |
| ccctcactcg | gcgcgccagt | cctccgatag | actgcgtcgc | ccgggtaccc | gtattcccaa | 420 |
| taaagcctct | tgctgtttgc | atccgaatcg | tggactcgct | gatccttggg | agggtctcct | 480 |
| cagattgatt | gactgcccac | ctcggggtc | tttcatttgg | aggttccacc | gagatttgga | 540 |
| gacccctgcc | cagggaccac | cgaccccccc | gccgggaggt | aagctggcca | gcggtcgttt | 600 |
| cgtgtctgtc | tctgtctttg | tgcgtgtttg | tgccggcatc | taatgtttgc | gcctgcgtct | 660 |
| gtactagtta | gctaactagc | tctgtatctg | gcggacccgt | ggtggaactg | acgagttctg | 720 |
| aacacccggc | cgcaaccctg | ggagacgtcc | cagggacttt | gggggccgtt | tttgtggccc | 780 |
| gacctgagga | agggagtcga | tgtggaatcc | gaccccgtca | ggatatgtgg | ttctggtagg | 840 |
| agacgagaac | ctaaaacagt | tcccgcctcc | gtctgaattt | ttgctttcgg | tttggaaccg | 900 |
| aagccgcgcg | tcttgtctgc | tgcagcgctg | cagcatcgtt | ctgtgttgtc | tctgtctgac | 960 |
| tgtgtttctg | tatttgtctg | aaaattaggg | ccagactgtt | accactccct | taagtttgac | 1020 |
| cttaggtcac | tggaaagatg | tcgagcggat | cgctcacaac | cagtcggtag | atgtcaagaa | 1080 |
| gagacgttgg | gttaccttct | gctctgcaga | atggccaacc | tttaacgtcg | gatggccgcg | 1140 |
| agacggcacc | tttaaccgag | acctcatcac | ccaggttaag | atcaaggtct | tttcacctgg | 1200 |
| cccgcatgga | cacccagacc | aggtccccta | tcgtgacc | tgggaagcct | ggcttttga | 1260 |
| ccccctccc | tgggtcaagc | cctttgtaca | ccctaagcct | ccgcctcctc | ttcctccatc | 1320 |
| cgccccgtct | ctcccccttg | aacctcctcg | ttcgaccccg | cctcgatcct | ccctttatcc | 1380 |
| agccctcact | ccttctctag | gcgccggcgg | ccgccgccac | catgggatcg | gccattgaac | 1440 |
| aagatggatt | gcacgcaggt | tctccggccg | cttgggtgga | gaggctattc | ggctatgact | 1500 |
| gggcacaaca | gacaatcggc | tgctctgatg | ccgccgtgtt | ccggctgtca | gcgcaggggc | 1560 |
| gcccggttct | ttttgtcaag | accgacctgt | ccggtgccct | gaatgaactg | caggacgagg | 1620 |
| cagcgcggct | atcgtggctg | gccacgacgg | gcgttccttg | cgcagctgtg | ctcgacgttg | 1680 |
| tcactgaagc | gggaagggac | tggctgctat | tgggcgaagt | gccggggcag | gatctcctgt | 1740 |
| catctcacct | tgctcctgcc | gagaaagtat | ccatcatggc | tgatgcaatg | cggcggctgc | 1800 |
| atacgcttga | tccggctacc | tgcccattcg | accaccaagc | gaaacatcgc | atcgagcgag | 1860 |
| cacgtactcg | gatggaagcc | ggtcttgtcg | atcaggatga | tctggacgaa | gagcatcagg | 1920 |
| ggctcgcgcc | agccgaactg | ttcgccaggc | tcaaggcgcg | catgcccgac | ggcgaggatc | 1980 |
| tcgtcgtgac | ccatggcgat | gcctgcttgc | cgaatatcat | ggtggaaaat | ggccgctttt | 2040 |
| ctggattcat | cgactgtggc | cggctgggtg | tggcggaccg | ctatcaggac | atagcgttgg | 2100 |
| ctacccgtga | tattgctgaa | gagcttggcg | gcgaatgggc | tgaccgcttc | ctcgtgcttt | 2160 |
| acggtatcgc | cgctcccgat | tcgcagcgca | tcgccttcta | tcgccttctt | gacgagttct | 2220 |

```
tctgagcggc cgcgaattcg tcgacgtgca tgcacgctca ttgcccatcg ctatccctgc    2280
ctctcctgct ggcgctcccc gggaggtgac ttcaagggga ccgcaggacc acctcggggg    2340 tgggggagg  gctgcacacg cggaccccgc tcccctccc  caacaaagca ctgtggaatc    2400 aaaaagggg  gaggggggat ggaggggcgc gtcacacccc cgcccacac  cctcacctcg    2460 aggtgagccc cacgttctgc ttcactctcc ccatctcccc ccctcccca  ccccaatttt    2520 tgtatttatt tattttttaa ttattttgtg cagcgatggg ggcggggggg ggggggcgc    2580 gcgccaggcg gggcggggcg gggcgagggg cggggcgggg cgaggcggag aggtgcggcg    2640
gcagccaatc agagcggcgc gctccgaaag tttccttta  tggcgaggcg gcggcggcgg    2700
cggccctata aaagcgaag  cgcgcggcgg gcgggagtcg ctgcgttgtc gacggatcct    2760
cgagctgcag aagctttcgc gaatcgataa aataaaagat tttatttagt ctccagaaaa    2820 agggggaat  gaaagacccc acctgtaggt ttggcaagct agcttaagta acgccatttt    2880
gcaaggcatg gaaatacat  aactgagaat agagaagttc agatcaaggt taggaacaga    2940
gagacagcag aatatgggcc aaacaggata tctgtggtaa gcagttcctg ccccggctca    3000
gggccaagaa cagatggtcc ccagatgcgg tcccgccctc agcagtttct agagaaccat    3060
cagatgtttc cagggtgccc caaggacctg aaatgaccct gtgccttatt tgaactaacc    3120
aatcagttcg cttctcgctt ctgttcgcgc gcttctgctc cccgagctca ataaaagagc    3180
ccacaacccc tcactcggcg cgccagtcct ccgatagact gcgtcgcccg ggtacccgtg    3240
tatccaataa accctcttgc agttgcatcc gacttgtggt ctcgctgttc cttgggaggg    3300
tctcctctga gtgattgact acccgtcagc ggggtctttt caggcctctg cattaatgaa    3360
tcggccaacg cgcggggaga ggcggtttgc gtattgggcg ctcttccgct tcctcgctca    3420
ctgactcgct gcgctcggtc gttcggctgc ggcgagcggt atcagctcac tcaaaggcgg    3480
taatacggtt atccacagaa tcaggggata acgcaggaaa gaacatgtga gcaaaaggcc    3540
agcaaaaggc caggaaccgt aaaaaggccg cgttgctggc gtttttccat aggctccgcc    3600
cccctgacga gcatcacaaa aatcgacgct caagtcagag gtggcgaaac ccgacaggac    3660
tataaagata ccaggcgttt ccccctggaa gctccctcgt gcgctctcct gttccgaccc    3720
tgccgcttac cggatacctg tccgcctttc tcccttcggg aagcgtggcg ctttctcaat    3780
gctcacgctg taggtatctc agttcggtgt aggtcgttcg ctccaagctg ggctgtgtgc    3840
acgaaccccc cgttcagccc gaccgctgcg ccttatccgg taactatcgt cttgagtcca    3900
acccggtaag acacgactta tcgccactgg cagcagccac tggtaacagg attagcagag    3960
cgaggtatgt aggcggtgct acagagttct tgaagtggtg gcctaactac ggctacacta    4020
gaaggacagt atttggtatc tgcgctctgc tgaagccagt taccttcgga aaaagagttg    4080
gtagctcttg atccggcaaa caaccaccg  ctggtagcgg tggttttttt gtttgcaagc    4140
agcagattac gcgcagaaaa aaaggatctc aagaagatcc tttgatcttt tctacggggt    4200
ctgacgctca gtggaacgaa aactcacgtt aagggatttt ggtcatgaga ttatcaaaaa    4260
ggatcttcac ctagatcctt ttaaattaaa aatgaagttt taaatcaatc taaagtatat    4320
atgagtaaac ttggtctgac agttaccaat gcttaatcag tgaggcacct atctcagcga    4380
tctgtctatt tcgttcatcc atagttgcct gactccccgt cgtgtagata actacgatac    4440
gggagggctt accatctggc cccagtgctg caatgatacc gcgagaccca cgctcaccgg    4500
ctccagattt atcagcaata aaccagccag ccggaagggc cgagcgcaga agtggtcctg    4560
caactttatc cgcctccatc cagtctatta attgttgccg ggaagctaga gtaagtagtt    4620
```

```
cgccagttaa tagtttgcgc aacgttgttg ccattgctac aggcatcgtg gtgtcacgct    4680
cgtcgtttgg tatggcttca ttcagctccg gttcccaacg atcaaggcga gttacatgat    4740
cccccatgtt gtgcaaaaaa gcggttagct ccttcggtcc tccgatcgtt gtcagaagta    4800
agttggccgc agtgttatca ctcatggtta tggcagcact gcataattct cttactgtca    4860
tgccatccgt aagatgcttt tctgtgactg gtgagtactc aaccaagtca ttctgagaat    4920
agtgtatgcg gcgaccgagt tgctcttgcc cggcgtcaat acgggataat accgcgccac    4980
atagcagaac tttaaaagtg ctcatcattg gaaaacgttc ttcggggcga aaactctcaa    5040
ggatcttacc gctgttgaga tccagttcga tgtaacccac tcgtgcaccc aactgatctt    5100
cagcatcttt tactttcacc agcgtttctg ggtgagcaaa acaggaagg  caaaatgccg    5160 caaaaaaggg aataagggcg acacggaaat gttgaatact catactcttc cttttcaat    5220 attattgaag catttatcag ggttattgtc tcatgagcgg atacatattt gaatgtattt    5280
agaaaaataa acaaataggg gttccgcgca catttccccg aaaagtgcca cctgacgtct    5340
aagaaaccat tattatcatg acattaacct ataaaaatag gcgtatcacg aggccctttc    5400
gtctcgcgcg tttcggtgat gacggtgaaa acctctgaca catgcagctc ccggagacgg    5460
tcacagcttg tctgtaagcg gatgccggga gcagacaagc ccgtcagggc gcgtcagcgg    5520
gtgttggcgg gtgtcggggc tggcttaact atgcggcatc agagcagatt gtactgagag    5580
tgcaccatat gcggtgtgaa ataccgcaca gatgcgtaag gagaaaatac cgcatcaggc    5640
aggcctgtta acttcgaacg attagtccaa tttgttaaag acaggatatc agtggtccag    5700
gctctagttt tgactcaaca atatcaccag ctgaagccta tagagtacga gccatagata    5760
aaataaaaga ttttatttag tctccagaaa aaggggggg                           5798
```

<210> SEQ ID NO 3
<211> LENGTH: 3747
<212> TYPE: DNA
<213> ORGANISM: Artificial
<220> FEATURE:
<223> OTHER INFORMATION: Plasmid vector pUCfEPO

<400> SEQUENCE: 3

```
tcgcgcgttt cggtgatgac ggtgaaaacc tctgacacat gcagctcccg gagacggtca      60
cagcttgtct gtaagcggat gccgggagca gacaagcccg tcagggcgcg tcagcgggtg     120
ttggcgggtg tcggggctgg cttaactatg cggcatcaga gcagattgta ctgagagtgc     180
accataaaat tgtaaacgtt aatattttgt taaaattcgc gttaaatttt tgttaaatca     240
gctcattttt taaccaatag gccgaaatcg gcaaaatccc ttataaatca aaagaatagc     300
ccgagatagg gttgagtgtt gttccagttt ggaacaagag tccactatta agaacgtgg      360 actccaacgt caaagggcga aaaccgtctc atcagggcga tggcccacta cgtgaaccat     420
cacccaaatc aagttttttg gggtcgaggt gccgtaaagc actaaatcgg aaccctaaag     480 ggagccccg  atttagagct tgacggggaa agccggcgaa cgtggcgaga aggaaggga      540 agaaagcgaa aggagcgggc gctagggcgc tggcaagtgt agcggtcacg ctgcgcgtaa     600
ccaccacacc cgccgcgctt aatgcgccgc tacagggcgc gtactatggt tgctttgacg     660
tatgcggtgt gaaataccgc acagatgcgt aaggagaaaa taccgcatca ggcgccattc     720
gccattcagg ctgcgcaact gttgggaagg gcgatcggtg cgggcctctt cgctattacg     780
ccagctggcg aaagggggat gtgctgcaag gcgattaagt tgggtaacgc cagggttttc     840
```

```
ccagtcacga cgttgtaaaa cgacggccag tgaattcgag ctcggtaccc ggggatcctc   900
tagagtcgac atggggtcgt gcgaatgtcc tgccctgctg cttctgctat ctttgctgct   960
gcttcccctg ggcctcccag tcctgggcgc ccccctcgc ctcatctgtg acagccgagt  1020
cctggagagg tacattctgg aggccaggga ggccgaaaat gtcacgatgg gctgtgctga  1080
aggctgcagc ttcagtgaga atatcactgt cccagacacc aaggtcaact tctatacctg  1140
gaagaggatg gacgtcgggc agcaggctgt ggaagtctgg cagggcctcg ccctgctctc  1200
agaagccatc ctgcggggcc aggccctgct ggccaactcc tcccagccat ctgagaccct  1260
gcagctgcat gtggataaag ccgtcagcag cctgcgcagc ctcacctccc tgcttcgggc  1320
actgggagcc cggaaggaag ccacctccct tccagaggca acctctgctg ctccactccg  1380
aacattcact gtcgatactt tgtgcaaact tttccgaatc tactccaact tcctgcgggg  1440
aaagctgacg ctgtacacag gggaggcctg ccgaagagga gacaggtgag tcgacctgca  1500
ggcatgcaag cttggcgtaa tcatggtcat agctgtttcc tgtgtgaaat tgttatccgc  1560
tcacaattcc acaacata cgagccgaa gcataaagtg taaagcctgg ggtgcctaat  1620
gagtgagcta actcacatta attgcgttgc gctcactgcc cgctttccag tcgggaaacc  1680
tgtcgtgcca gctgcattaa tgaatcggcc aacgcgcggg gagaggcggt ttgcgtattg  1740
ggcgctcttc cgcttcctcg ctcactgact cgctgcgctc ggtcgttcgg ctgcggcgag  1800
cggtatcagc tcactcaaag gcggtaatac ggttatccac agaatcaggg gataacgcag  1860
gaaagaacat gtgagcaaaa ggccagcaaa aggccaggaa ccgtaaaaag gccgcgttgc  1920
tggcgttttt ccataggctc cgcccccctg acgagcatca caaaaatcga cgctcaagtc  1980
agaggtggcg aaacccgaca ggactataaa gataccaggc gtttccccct ggaagctccc  2040
tcgtgcgctc tcctgttccg accctgccgc ttaccggata cctgtccgcc tttctccctt  2100
cgggaagcgt ggcgctttct catagctcac gctgtaggta tctcagttcg gtgtaggtcg  2160
ttcgctccaa gctgggctgt gtgcacgaac cccccgttca gcccgaccgc tgcgccttat  2220
ccggtaacta tcgtcttgag tccaacccgg taagacacga cttatcgcca ctggcagcag  2280
ccactggtaa caggattagc agagcgaggt atgtaggcgg tgctacagag ttcttgaagt  2340
ggtggcctaa ctacggctac actagaagga cagtatttgg tatctgcgct ctgctgaagc  2400
cagttacctt cggaaaaaga gttggtagct cttgatccgg caaacaaacc accgctggta  2460
gcggtggttt ttttgtttgc aagcagcaga ttacgcgcag aaaaaaagga tctcaagaag  2520
atcctttgat cttttctacg ggtctgacgc tcagtggaa cgaaaactca cgttaaggga  2580
ttttggtcat gagattatca aaaaggatct tcacctagat ccttttaaat taaaaatgaa  2640
gttttaaatc aatctaaagt atatatgagt aaacttggtc tgacagttac caatgcttaa  2700
tcagtgaggc acctatctca gcgatctgtc tatttcgttc atccatagtt gcctgactcc  2760
ccgtcgtgta gataactacg atacgggagg gcttaccatc tggccccagt gctgcaatga  2820
taccgcgaga cccacgctca ccggctccag atttatcagc aataaaccag ccagccggaa  2880
gggccgagcg cagaagtggt cctgcaactt tatccgcctc catccagtct attaattgtt  2940
gccgggaagc tagagtaagt agttcgccag ttaatagttt cgcaacgtt gttgccattg  3000
ctacaggcat cgtggtgtca cgctcgtcgt ttggtatggc ttcattcagc tccggttccc  3060
aacgatcaag gcgagttaca tgatccccca tgttgtgcaa aaaagcggtt agctccttcg  3120
gtcctccgat cgttgtcaga agtaagttgg ccgcagtgtt atcactcatg gttatggcag  3180
cactgcataa ttctcttact gtcatgccat ccgtaagatg cttttctgtg actggtgagt  3240
```

```
actcaaccaa gtcattctga gaatagtgta tgcggcgacc gagttgctct tgcccggcgt    3300
caatacggga taataccgcg ccacatagca gaactttaaa agtgctcatc attggaaaac    3360
gttcttcggg gcgaaaactc tcaaggatct taccgctgtt gagatccagt tcgatgtaac    3420
ccactcgtgc acccaactga tcttcagcat cttttacttt caccagcgtt tctgggtgag    3480
caaaaacagg aaggcaaaat gccgcaaaaa agggaataag ggcgacacgg aaatgttgaa    3540
tactcatact cttccttttt caatattatt gaagcattta tcagggttat tgtctcatga    3600
gcggatacat atttgaatgt atttagaaaa ataaacaaat aggggttccg cgcacatttc    3660
cccgaaaagt gccacctgac gtctaagaaa ccattattat catgacatta acctataaaa    3720
ataggcgtat cacgaggccc tttcgtc                                       3747

<210> SEQ ID NO 4
<211> LENGTH: 47
<212> TYPE: DNA
<213> ORGANISM: Artificial
<220> FEATURE:
<223> OTHER INFORMATION: Primer for producing pMSCVneobactfEPO

<400> SEQUENCE: 4
agccaagctt accatggggt cgtgcgaatg tcctgccctg ctgcttc                  47

<210> SEQ ID NO 5
<211> LENGTH: 38
<212> TYPE: DNA
<213> ORGANISM: Artificial
<220> FEATURE:
<223> OTHER INFORMATION: Primer for producing pMSCVneobactfEPO

<400> SEQUENCE: 5
cgataagctt acgcgttcac ctgtctcctc ttcggcag                            38

<210> SEQ ID NO 6
<211> LENGTH: 37
<212> TYPE: DNA
<213> ORGANISM: Artificial
<220> FEATURE:
<223> OTHER INFORMATION: Primer for producing pMSCVneobactfEPOwpre

<400> SEQUENCE: 6
ccatcgataa tcaacctctg gattacaaaa tttgtga                             37

<210> SEQ ID NO 7
<211> LENGTH: 22
<212> TYPE: DNA
<213> ORGANISM: Artificial
<220> FEATURE:
<223> OTHER INFORMATION: Primer for producing pMSCVneobactfEPOwpre

<400> SEQUENCE: 7
ccatcgatca ggcggggagg cg                                             22
```

The invention claimed is:

1. A method for producing a polyethylene glycol (PEG)-modified mammalian erythropoietin (EPO), the method comprising:
   extracting a mammalian EPO from an egg laid by a transgenic chicken; and adding PEG to the EPO,
   wherein the transgenic chicken comprises a nucleic acid sequence encoding the EPO operably linked to an oviduct-specific promoter.

2. The method of claim 1, wherein the EPO is a human or feline EPO.

3. The method of claim 1, wherein the EPO is:
   (a) a protein having the amino acid sequence of SEQ ID NO: 1, or
   (b) a protein having at least a part of the amino acid sequence of SEQ ID NO:1,
   wherein the EPO does not have EPO activity in vivo in a mammal before adding the PEG, and wherein the EPO has erythropoietin activity in vivo in a mammal after adding the PEG.

4. The method of claim 1, wherein the PEG has a weight average molecular weight of 5 to 40 kDa.

5. The method of claim 1, wherein the number of PEG molecules added is 2 or more.

6. The method of claim 1, wherein the PEG is a succinimidyl ester derivative of PEG.

7. The method of claim 1, wherein the extracting is performed by purifying the EPO from egg white of the egg laid by the transgenic chicken.

8. The method of claim 7, wherein the purifying the EPO is performed by a column technique or filtration after diluting the egg white.

9. The method of claim 8, wherein the egg white is diluted 2 to 10 times by pure water or an equilibrated salt solution.

* * * * *